United States Patent
Mackintosh

(10) Patent No.: US 9,828,621 B2
(45) Date of Patent: Nov. 28, 2017

(54) ANOMALOUS SIGNAL ERROR TRAP FOR AN ANALYTE MEASUREMENT DETERMINED FROM A SPECIFIED SAMPLING TIME DERIVED FROM A SENSED PHYSICAL CHARACTERISTIC OF THE SAMPLE CONTAINING THE ANALYTE

(71) Applicant: LifeScan Scotland Limited, Inverness-shire (GB)

(72) Inventor: Stephen Mackintosh, Inverness (GB)

(73) Assignee: LifeScan Scotland Limited, Inverness (GB)

( * ) Notice: Subject to any disclaimer, the term of this patent is extended or adjusted under 35 U.S.C. 154(b) by 874 days.

(21) Appl. No.: 14/022,601

(22) Filed: Sep. 10, 2013

(65) Prior Publication Data
US 2015/0068922 A1 Mar. 12, 2015

Related U.S. Application Data

(60) Provisional application No. 61/875,785, filed on Sep. 10, 2013.

(51) Int. Cl.
*G01N 27/327* (2006.01)
*G01N 27/04* (2006.01)
*C12Q 1/00* (2006.01)

(52) U.S. Cl.
CPC ......... *C12Q 1/006* (2013.01); *G01N 27/3274* (2013.01)

(58) Field of Classification Search
None
See application file for complete search history.

(56) References Cited

U.S. PATENT DOCUMENTS

| | | |
|---|---|---|
| 4,919,770 A | 4/1990 | Preidel et al. |
| 5,352,351 A | 10/1994 | White et al. |
| 6,179,979 B1 | 1/2001 | Hodges et al. |
| 6,193,873 B1 | 2/2001 | Ohara et al. |
| 6,284,125 B1 | 9/2001 | Hodges et al. |
| 6,413,410 B1 | 7/2002 | Hodges et al. |
| 6,475,372 B1 | 11/2002 | Ohara et al. |
| 6,716,577 B1 | 4/2004 | Yu et al. |
| 6,749,887 B1 | 6/2004 | Dick et al. |

(Continued)

FOREIGN PATENT DOCUMENTS

| | | |
|---|---|---|
| EP | 1541998 A1 | 6/2005 |
| EP | 1804048 B1 | 5/2010 |

(Continued)

OTHER PUBLICATIONS

Kohma, Takyua, et al., "Ultilization of AC Impedance Measurements for Electrochemical Glucose Sensing Glucose Oxidase to Improve Detection Selectivity," Bull. Chem. Soc. Jpn., vol. 80, No. 1, 158-165, 2007.

(Continued)

*Primary Examiner* — Luan Van
*Assistant Examiner* — Steven E Rosenwald

(57) ABSTRACT

Various embodiments for a method that allow for a more accurate analyte concentration with a biosensor by determining at least one physical characteristic of the sample and determining whether at least one output transient signal of the biosensor is erroneous by monitoring the biosensor and flagging an error if the signal outputs of the biosensor do not meet certain criteria.

19 Claims, 20 Drawing Sheets

(56) References Cited

U.S. PATENT DOCUMENTS

| | | |
|---|---|---|
| 6,860,421 B2 | 3/2005 | Lo Duca |
| 6,863,801 B2 | 3/2005 | Hodges et al. |
| 7,045,046 B2 | 5/2006 | Chambers et al. |
| 7,258,769 B2 | 8/2007 | Cui et al. |
| 7,291,256 B2 | 11/2007 | Teodorczyk et al. |
| 7,498,132 B2 | 3/2009 | Yu et al. |
| 7,972,861 B2 | 7/2011 | Deng et al. |
| 2004/0079652 A1 | 4/2004 | Vreeke et al. |
| 2008/0083618 A1 | 4/2008 | Neel et al. |
| 2009/0194432 A1 | 8/2009 | Deng |
| 2009/0223834 A1 | 9/2009 | Cai et al. |
| 2009/0236237 A1 | 9/2009 | Shinno et al. |
| 2010/0005865 A1 | 1/2010 | Miura |
| 2010/0206749 A1 | 8/2010 | Choi |
| 2010/0276303 A1 | 11/2010 | Fujiwara et al. |
| 2010/0283488 A1 | 11/2010 | Nakamura et al. |
| 2011/0020852 A1* | 1/2011 | Kojima ............. A61B 5/1405 435/14 |
| 2014/0027308 A1* | 1/2014 | Harrison ............ A61B 5/14532 205/777.5 |

FOREIGN PATENT DOCUMENTS

| | | |
|---|---|---|
| WO | WO 2006/070200 A1 | 7/2006 |
| WO | 2013030369 A1 | 3/2013 |
| WO | 2013030375 A1 | 3/2013 |
| WO | WO 2013/098563 A1 | 7/2013 |
| WO | WO 2013/098564 A1 | 7/2013 |
| WO | WO 2013/098565 A1 | 7/2013 |

OTHER PUBLICATIONS

Wegener, Joachim, et al., "Electric Cell-Substrate Impedance Sensing (ECIS) as a Noninvasive Means to Monitor the Kinetics of Cell Spreading to Artificial Surfaces," Experimental Cell Research, 259, 258-166, 2000.

International Search Report and Written Opinion issued in related International Patent Application No. PCT/EP2014/069163, dated Nov. 4, 2014, 15 pages.

* cited by examiner

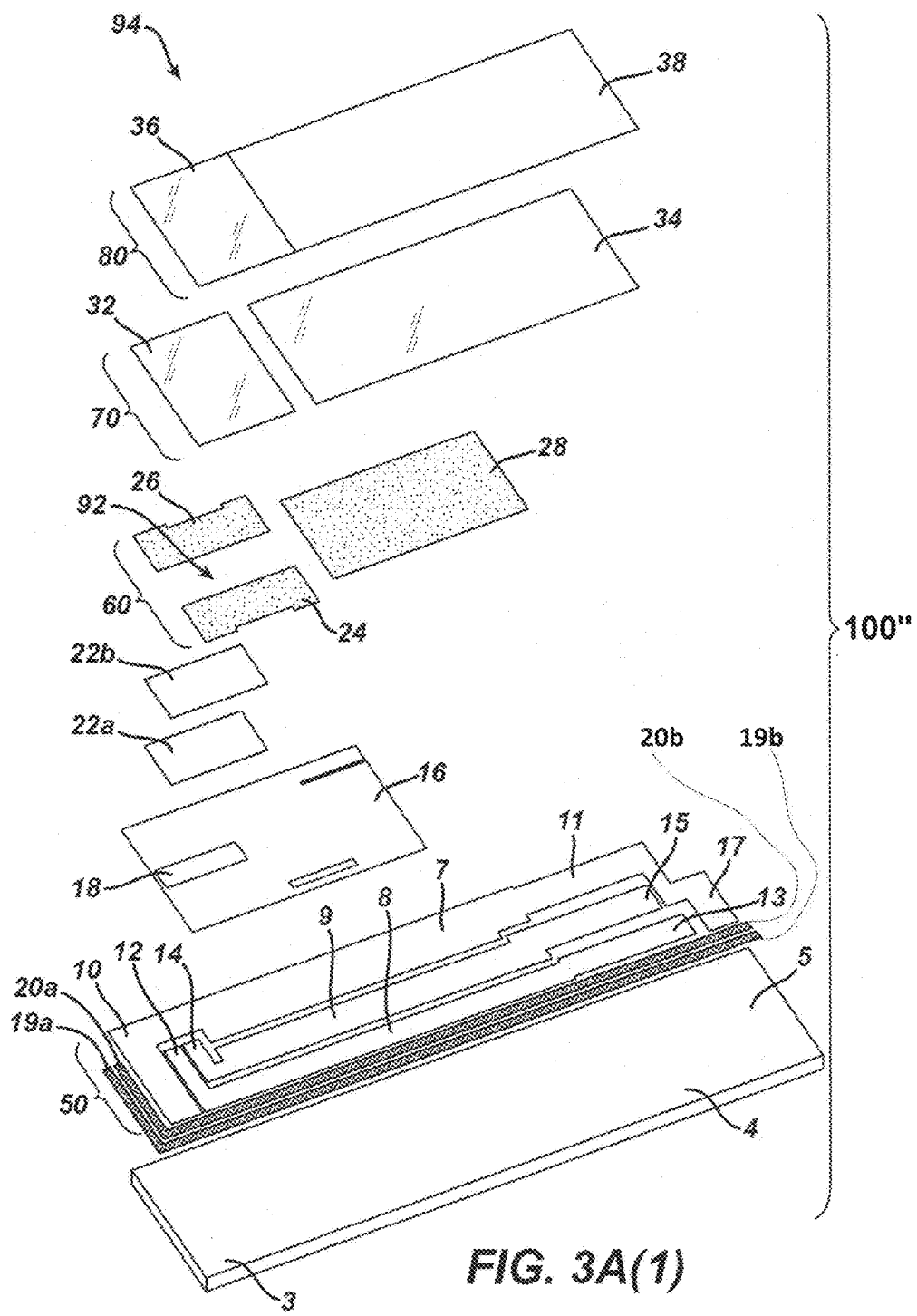
FIG. 3A(1)

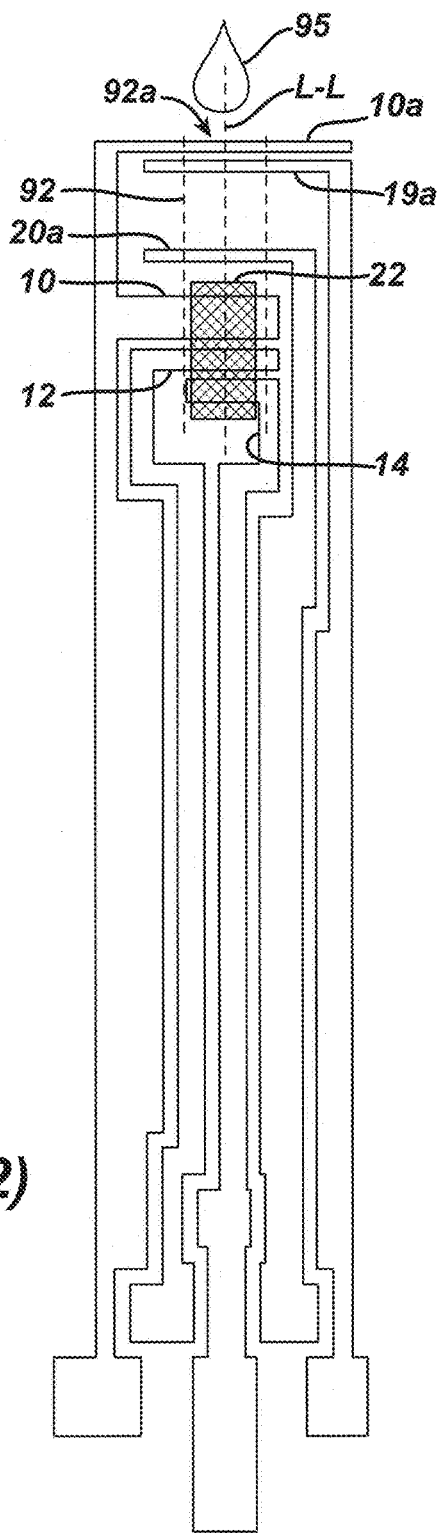
FIG. 3A(2)

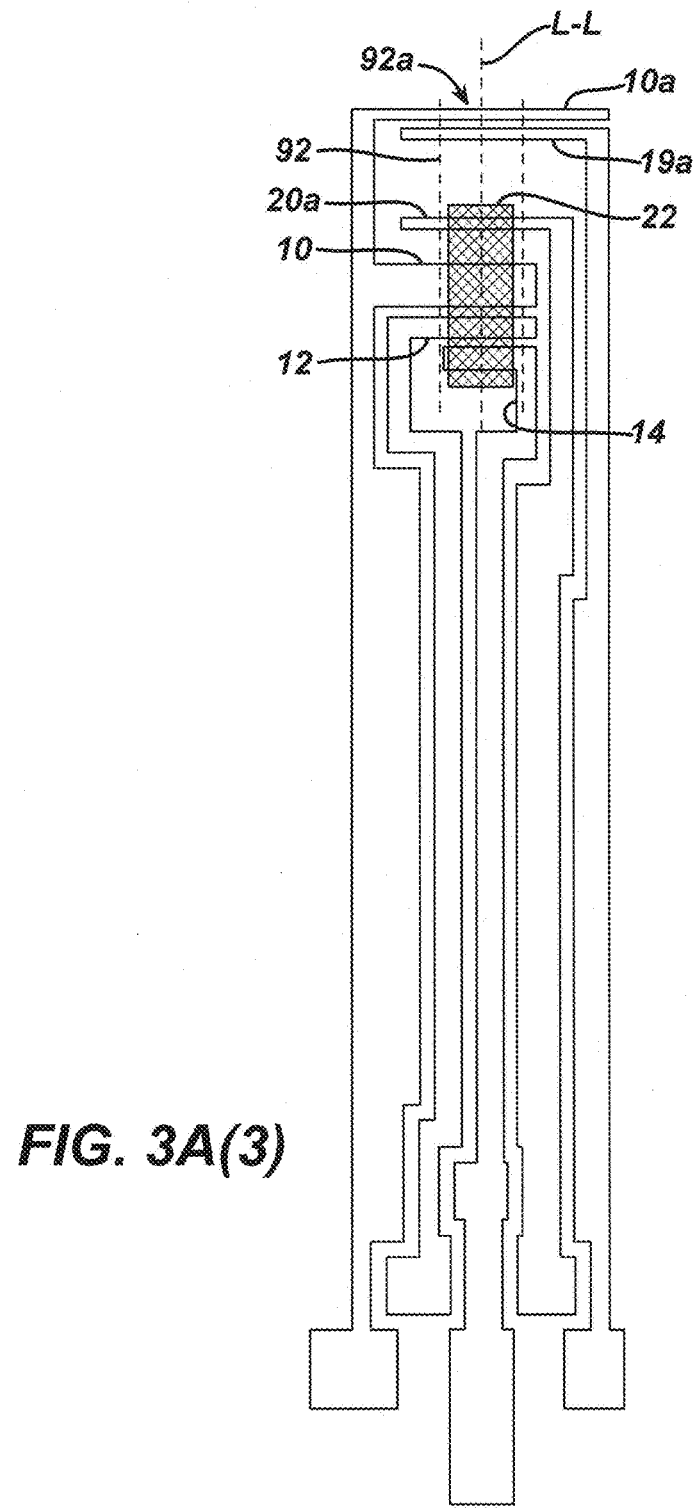
FIG. 3A(3)

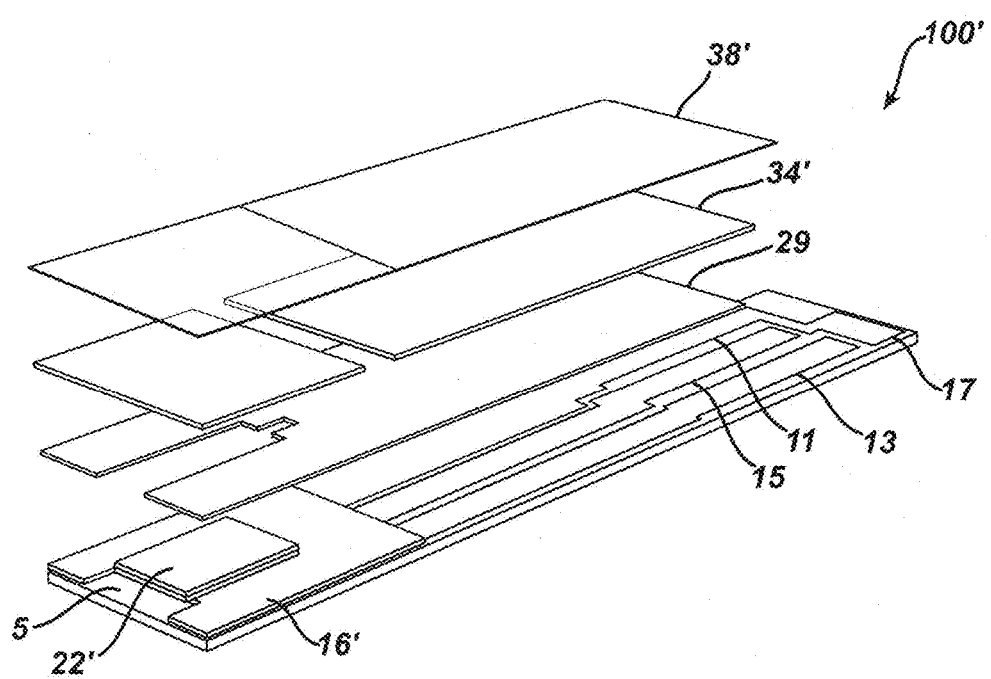
FIG. 3A(4)

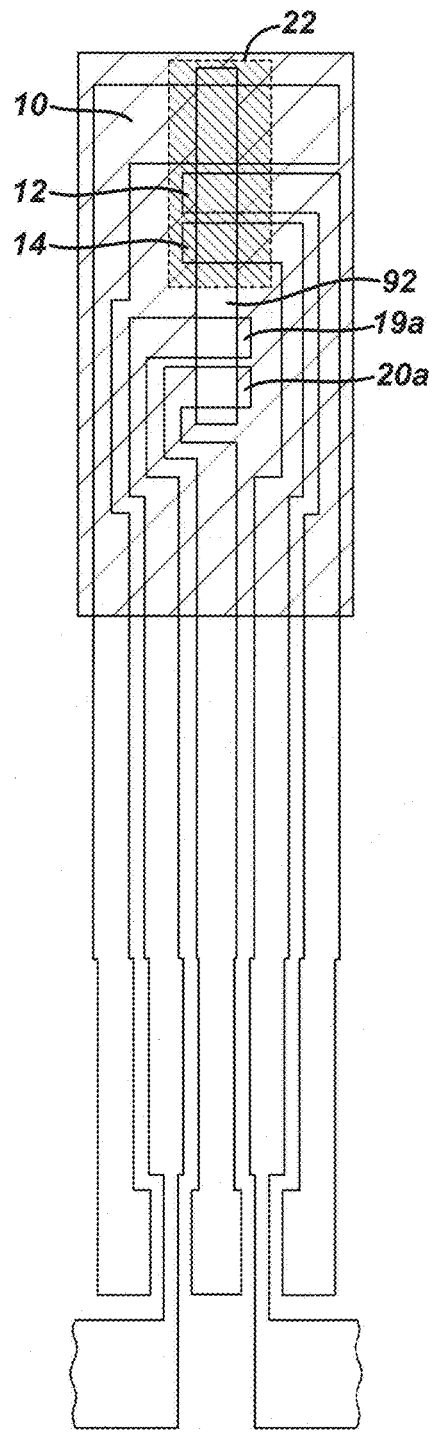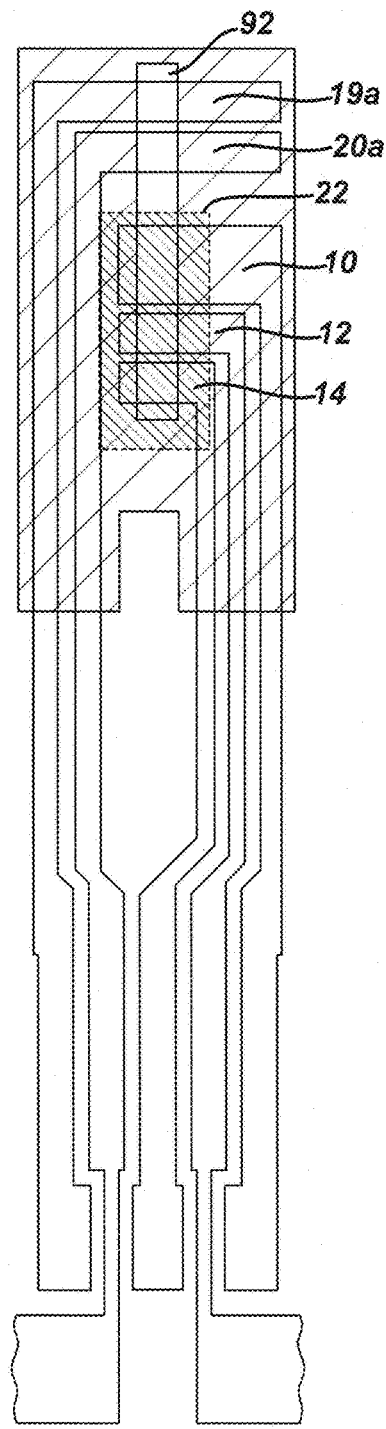
*FIG. 3D*  *FIG. 3E*

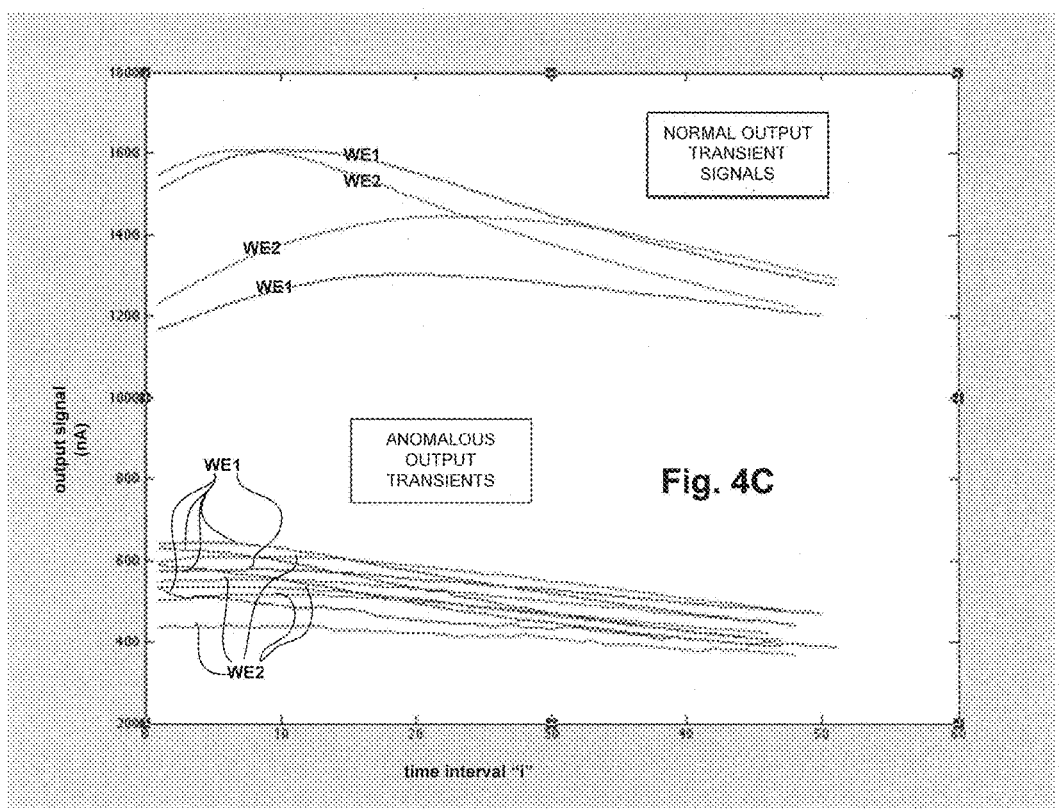

ANOMALOUS SIGNAL ERROR TRAP FOR AN ANALYTE MEASUREMENT DETERMINED FROM A SPECIFIED SAMPLING TIME DERIVED FROM A SENSED PHYSICAL CHARACTERISTIC OF THE SAMPLE CONTAINING THE ANALYTE

PRIORITY

This application claims priority to prior filed provisional application Ser. No. 61/875,785 filed on Sep. 10, 2013, in which the entirety of the prior filed application is incorporated by reference herein this application.

BACKGROUND

Electrochemical glucose test strips, such as those used in the OneTouch® Ultra® whole blood testing kit, which is available from LifeScan, Inc., are designed to measure the concentration of glucose in a physiological fluid sample from patients with diabetes. The measurement of glucose can be based on the selective oxidation of glucose by the enzyme glucose oxidase (GO). The reactions that can occur in a glucose test strip are summarized below in Equations 1 and 2.

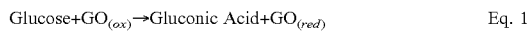

Glucose+$GO_{(ox)}$→Gluconic Acid+$GO_{(red)}$      Eq. 1

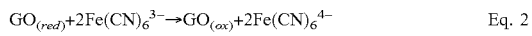

$GO_{(red)}$+2$Fe(CN)_6^{3-}$→$GO_{(ox)}$+2$Fe(CN)_6^{4-}$      Eq. 2

As illustrated in Equation 1, glucose is oxidized to gluconic acid by the oxidized form of glucose oxidase ($GO_{(ox)}$). It should be noted that $GO_{(ox)}$ may also be referred to as an "oxidized enzyme." During the reaction in Equation 1, the oxidized enzyme $GO_{(ox)}$ is converted to its reduced state, which is denoted as $GO_{(red)}$ (i.e., "reduced enzyme"). Next, the reduced enzyme $GO_{(red)}$ is re-oxidized back to $GO_{(ox)}$ by reaction with $Fe(CN)_6^{3-}$ (referred to as either oxidized mediator or ferricyanide) as illustrated in Equation 2. During the re-generation of $GO_{(red)}$ back to its oxidized state $GO_{(ox)}$, $Fe(CN)_6^{3-}$ is reduced to $Fe(CN)_6^{4-}$ (referred to as either reduced mediator or ferrocyanide).

When the reactions set forth above are conducted with a test signal applied between two electrodes, a test current can be created by the electrochemical re-oxidation of the reduced mediator at the electrode surface. Thus, since, in an ideal environment, the amount of ferrocyanide created during the chemical reaction described above is directly proportional to the amount of glucose in the sample positioned between the electrodes, the test current generated would be proportional to the glucose content of the sample. A mediator, such as ferricyanide, is a compound that accepts electrons from an enzyme such as glucose oxidase and then donates the electrons to an electrode. As the concentration of glucose in the sample increases, the amount of reduced mediator formed also increases; hence, there is a direct relationship between the test current, resulting from the re-oxidation of reduced mediator, and glucose concentration. In particular, the transfer of electrons across the electrical interface results in the flow of a test current (2 moles of electrons for every mole of glucose that is oxidized). The test current resulting from the introduction of glucose can, therefore, be referred to as a glucose signal.

Electrochemical biosensors may be adversely affected by the presence of certain blood components that may undesirably affect the measurement and lead to inaccuracies in the detected signal. This inaccuracy may result in an inaccurate glucose reading, leaving the patient unaware of a potentially dangerous blood sugar level, for example. As one example, the blood hematocrit level (i.e. the percentage of the amount of blood that is occupied by red blood cells) can erroneously affect a resulting analyte concentration measurement.

Variations in a volume of red blood cells within blood can cause variations in glucose readings measured with disposable electrochemical test strips. Typically, a negative bias (i.e., lower calculated analyte concentration) is observed at high hematocrit, while a positive bias (i.e., higher calculated analyte concentration as compared to referential analyte concentration) is observed at low hematocrit. At high hematocrit, for example, the red blood cells may impede the reaction of enzymes and electrochemical mediators, reduce the rate of chemistry dissolution since there is less plasma volume to solvate the chemical reactants, and slow diffusion of the mediator. These factors can result in a lower than expected glucose reading as less signal is produced during the electrochemical process. Conversely, at low hematocrit, fewer red blood cells may affect the electrochemical reaction than expected, and a higher measured signal can result. In addition, the physiological fluid sample resistance is also hematocrit dependent, which can affect voltage and/or current measurements.

Several strategies have been used to reduce or avoid hematocrit based variations on blood glucose. For example, test strips have been designed to incorporate meshes to remove red blood cells from the samples, or have included various compounds or formulations designed to increase the viscosity of red blood cells and attenuate the effect of low hematocrit on concentration determinations. Other test strips have included lysis agents and systems configured to determine hemoglobin concentration in an attempt to correct hematocrit. Further, biosensors have been configured to measure hematocrit by measuring an electrical response of the fluid sample via alternating current signals or change in optical variations after irradiating the physiological fluid sample with light, or measuring hematocrit based on a function of sample chamber fill time. These sensors have certain disadvantages. A common technique of the strategies involving detection of hematocrit is to use the measured hematocrit value to correct or change the measured analyte concentration, which technique is generally shown and described in the following respective US Patent Application Publication Nos. 2010/0283488; 2010/0206749; 2009/0236237; 2010/0276303; 2010/0206749; 2009/0223834; 2008/0083618; 2004/0079652; 2010/0283488; 2010/0206749; 2009/0194432; or U.S. Pat. Nos. 7,972,861 and 7,258,769, all of which are incorporated by reference herein to this application.

SUMMARY OF THE DISCLOSURE

Applicant has devised systems and methods that allow for determination of an error the output signal transient of the biosensor. In one aspect, applicant has devised an analyte measurement system that includes a test strip and an analyte meter. The test strip includes a substrate, a plurality of electrodes connected to respective electrode connectors. The analyte meter includes a housing with a test strip port connector configured to connect to the respective electrode connectors of the test strip and a microprocessor in electrical communication with the test strip port connector to apply electrical signals or sense electrical signals from the plurality of electrodes. In the meter, the microprocessor is configured to: apply a first signal to the plurality of electrodes so that a physical characteristic of a fluid sample is determined; estimate an analyte concentration based on a signal output at a predetermined sampling time during a test sequence; apply a second signal to a first electrode and a second electrode of the plurality of electrodes at a specified sampling time point or interval during the test sequence dictated by the determined physical characteristic; measure a signal output at a plurality of time points including the specified sampling time for each of the first and second electrodes; measure a signal output at the predetermined sampling time for each of the first and second electrodes; evaluate, for each of the first and second electrodes, whether a difference between respective magnitudes of the signal output at the specified sampling time and the predetermined sampling time is less than a predetermined threshold; if the difference for each electrode is equal to or greater than the predetermined threshold then determine or calculate the analyte concentration from the signal outputs of the first and second electrodes at the specified sampling time and annunciate the analyte concentration; and if the difference in magnitude for each electrode is less than the predetermined threshold then annunciate an error.

In yet a second aspect, applicant has devised an analyte measurement system that includes a test strip and an analyte meter. The test strip includes a substrate, a plurality of electrodes connected to respective electrode connectors. The analyte meter includes a housing with a test strip port connector configured to connect to the respective electrode connectors of the test strip and a microprocessor in electrical communication with the test strip port connector to apply electrical signals or sense electrical signals from the plurality of electrodes. In the meter, microprocessor is configured to: apply a first signal to the plurality of electrodes so that a physical characteristic of a fluid sample is determined; estimate an analyte concentration based on a predetermined sampling time during a test sequence; apply a second signal to a first electrode and a second electrode of the plurality of electrodes at a specified sampling time point or interval during the test sequence dictated by the determined physical characteristic; measure a signal output at a plurality of time points including the specified sampling time and the predetermined sampling time for each of the first and second electrodes; evaluate, for each of the first and second electrodes, whether a difference in a magnitude of the signal output at the specified sampling time and the predetermined time is less than a predetermined threshold; if the difference in magnitude for each electrode is less than the predetermined threshold then set an error flag as active; determine or calculate the analyte concentration from the signal outputs of the first and second electrodes at the specified sampling time; if the error flag is set then terminate the process; and if the difference in magnitude for each electrode is greater than the predetermined threshold then annunciate the analyte value.

In a third aspect, applicant has devised an analyte measurement system that includes a test strip and an analyte meter. The test strip includes a substrate, a plurality of electrodes connected to respective electrode connectors. The analyte meter includes a housing with a test strip port connector configured to connect to the respective electrode connectors of the test strip and a microprocessor in electrical communication with the test strip port connector to apply electrical signals or sense electrical signals from the plurality of electrodes. In the meter, the microprocessor is configured to: apply a first signal to the plurality of electrodes so that a physical characteristic of a fluid sample is determined; estimate an analyte concentration based on a predetermined sampling time during a test sequence; apply a second signal to a first electrode and a second electrode of the plurality of electrodes at a specified sampling time point or interval during the test sequence dictated by the determined physical characteristic; measure a signal output at a plurality of time points including the specified sampling time and the predetermined sampling time for each of the first and second electrodes; evaluate whether a magnitude of a difference between output signals at the specified sampling time and the predetermined sampling time for each working electrode is greater than a predetermined threshold and if true calculate an analyte concentration for the sample otherwise if false annunciate an error or set an error flag; and determine whether the magnitude of the output signal for each working electrode at an offset time interval before the specified sampling as less than the magnitude for the working electrode at the specified sampling time and if true annunciate an error or set an error flag active.

In a fourth aspect, applicant has devised method of determining current transient output error in a biosensor having a plurality of electrodes with first, second, third and fourth electrodes. The method can be achieved by: applying a first signal to the first and second electrodes; depositing a fluid sample proximate the first, second, third and fourth electrodes; applying a second signal to the third and fourth electrodes; determining a physical characteristic of the fluid sample from an output signal of the third and fourth electrodes; defining a specified sampling time based on the physical characteristic of the fluid sample; initiating an electrochemical reaction between the first and second electrodes and an analyte in a fluid sample to start a test sequence for a transformation of the analyte into an enzymatic-byproduct; measuring signal outputs at the specified sampling time and from a predetermined sampling from each of the first and second electrodes during the electrochemical reaction; evaluating, for each of the first and second electrodes, whether a difference in respective magnitudes of the output signal at the specified sampling time and the output signal at the predetermined sampling time is less than a predetermined threshold; if the evaluating is true then annunciate an output transient error and terminate the test sequence; if the evaluating step is false then calculating an analyte concentration representative of a quantity of analyte in the fluid sample from the signal outputs and annunciating the analyte concentration.

In yet a fifth aspect, applicant has devised a method of determining a transient output error in a biosensor. The biosensor has a plurality of electrodes with first, second, third and fourth electrodes provided with enzymes thereon. The method can be achieved by: depositing a fluid sample on a biosensor; causing the analyte in the sample to undergo an enzymatic reaction and start a test sequence; estimating an analyte concentration in the sample; measuring at least one physical characteristic of the sample; defining a specified sampling time from the start of the test sequence to sample output signals of the biosensor based on the estimated analyte concentration from the estimating step and at least one physical characteristic from the measuring step; sampling output signals from a first electrode and a second electrode of the biosensor at a plurality of time points including the specified sampling time; evaluating, for each of the first and second electrodes, whether a difference in respective magnitudes of the output signal at the specified sampling time and the output signal at the predetermined sampling time is less than a predetermined threshold; if the evaluating step is true then annunciating an error and terminating further processing; if the evaluating step is false then determining an analyte concentration from the sampled output signals of respective first and second electrodes at a plurality of time points including the specified sampling time.

In yet a sixth aspect, applicant has devised a method of determining a transient output error in a biosensor. The biosensor has a plurality of electrodes with first, second, third and fourth electrodes provided with enzymes thereon. The method can be achieved by: depositing a fluid sample on a biosensor; causing the analyte in the sample to undergo an enzymatic reaction and start a test sequence; estimating an analyte concentration in the sample; measuring at least one physical characteristic of the sample; defining a specified sampling time from the start of the test sequence to sample output signals of the biosensor based on the estimated analyte concentration from the estimating step and at least one physical characteristic from the measuring step; sampling output signals from a first electrode and a second electrode of the biosensor at a plurality of time points including the specified sampling time; evaluating, for each of the first and second electrodes, whether a difference in respective magnitudes of the output signal at the specified sampling time and the output signal at the predetermined sampling time is less than a predetermined threshold and if true for at least one of the working electrodes, annunciating an error or setting an error flag as active otherwise if the difference in respective magnitudes of the output signal at the specified sampling time and the output signal at the predetermined sampling time is equal to or greater than the predetermined threshold, then calculating the analyte concentration based on the magnitude of the output signal measured at the specified sampling time.

In yet a seventh aspect, applicant has devised a method of determining a transient output error in a biosensor. The biosensor has a plurality of electrodes with first, second, third and fourth electrodes provided with enzymes thereon. The method can be achieved by: depositing a fluid sample on a biosensor; causing the analyte in the sample to undergo an enzymatic reaction and start a test sequence; estimating an analyte concentration in the sample; measuring at least one physical characteristic of the sample; defining a specified sampling time from the start of the test sequence to sample output signals of the biosensor based on the estimated analyte concentration from the estimating step and at least one physical characteristic from the measuring step; sampling output signals from a first electrode and a second electrode of the biosensor at a plurality of time points including the specified sampling time; evaluating, for each of the first and second electrodes, whether a difference in respective magnitudes of the output signal at the specified sampling time and the output signal at the predetermined sampling time is less than a predetermined threshold; setting an error flag as active if the evaluating step is true; calculating the analyte concentration from the signal outputs of the first and second electrodes at the specified sampling time if the evaluating step is false; determining whether the error flag is active and if the error flag is not active then annunciating the analyte concentration otherwise if the error flag is active then prohibiting the annunciation of the analyte concentration.

Accordingly, in any of the embodiments described earlier, the following features may also be utilized in various combinations with the previously disclosed embodiments. For example, the plurality of electrodes may include four electrodes with the first and second electrodes to measure the analyte concentration and third and fourth electrodes to measure the physical characteristic; the first, second, third and fourth electrodes are disposed in the same chamber provided on the substrate; the first and second electrodes and third and fourth electrodes are disposed in respective two different chambers provided on the substrate; all of the electrodes are disposed on the same plane defined by the substrate; a reagent is disposed proximate the at least two other electrodes and no reagent is disposed on the third and fourth electrodes; the analyte concentration is determined from the second signal within about 10 seconds of a start of the test sequence and the predetermined threshold may include any value from about 10 to about 30; the specified sampling time is selected from a look-up table that includes a matrix in which different qualitative categories of the estimated analyte are set forth in the leftmost column of the matrix and different qualitative categories of the measured or estimated physical characteristic are set forth in the topmost row of the matrix and the sampling times are provided in the remaining cells of the matrix; the predetermined threshold is about 100 nanoamperes; the microcontroller determines the analyte concentration with an equation of the form:

$$G_0 = \left[\frac{I_T - \text{Intercept}}{\text{Slope}}\right]$$

where
$G_0$ represents an analyte concentration;
$I_T$ represents the output signals measured at the SpecifiedSamplingTime;
Slope represents the value obtained from calibration testing of a batch of test strips of which this particular strip comes from; and
Intercept represents the value obtained from calibration testing of a batch of test strips of which this particular strip comes from.

Moreover, in any of the embodiments described earlier, the following features may also be utilized in various combinations with the previously disclosed embodiments. For example, the microcontroller estimates the analyte concentration with an equation of the form:

$$G_{est} = \frac{(I_E - x_2)}{x_1}$$

where
$G_{est}$ represents the estimated analyte concentration;
$I_E$ is the signal measured at the predetermined sampling time;
$x_1$ may include a calibration slope of a particular batch of biosensors;
$x_2$ may include a calibration intercept of a particular batch of biosensors; and
in which the microcontroller determines the analyte concentration with an equation of the form:

$$G_o = \frac{(I_S - x_4)}{x_3}$$

where:
$G_O$ represents the analyte concentration;
$I_S$ may include the signal measured at the specified sampling time;

x₃ may include a calibration slope of a particular batch of biosensors; and x₄ may include the intercept of a particular batch of biosensors.

Furthermore, in each of the previously described methods, the following steps may also be utilized in various combinations with the previously disclosed embodiments. For example, the measuring may include applying a first signal to the sample to measure a physical characteristic of the sample; the causing step may include driving a second signal to the sample; the measuring may include evaluating an output signal from at least two electrodes of the biosensor at a point in time after the start of the test sequence, in which the point in time is set as a function of at least the measured or estimated physical characteristic; and the determining step may include calculating an analyte concentration from the measured output signal at said point in time; estimating an analyte concentration based on a predetermined sampling time point from the start of the test sequence; the defining may include selecting a defined time point based on both the measured or estimated physical characteristic and the estimated analyte concentration; estimating an analyte concentration based on a measurement of the output signal at a predetermined time; the predetermined time may include the predetermined sampling time from the start of the test sequence; the estimating may include comparing the estimated analyte concentration and the measured or estimated physical characteristic against a look-up table having different respective ranges of analyte concentration and physical characteristic of the sample indexed against different sample measurement times so that the point in time for measurement of the output from the sample of the second signal is obtained for the calculating step; the applying of the first signal and the driving of the second signal is sequential; the applying of the first signal overlaps with the driving of the second signal; the applying of the first signal may include directing an alternating signal to the sample so that a physical characteristic of the sample is determined from an output of the alternating signal from the sample; the applying of the first signal may include directing an electromagnetic signal to the sample so that a physical characteristic of the sample is determined from an output of the electromagnetic signal; the physical characteristic may include at least one of viscosity, hematocrit, temperature and density; the physical characteristic may include hematocrit and the analyte may include glucose; the directing may include driving first and second alternating signal at different respective frequencies in which a first frequency is lower than the second frequency; the first frequency is at least one order of magnitude lower than the second frequency; the first frequency may include any frequency in the range of about 10 kHz to about 250 kHz; 40; the sampling may include sampling the signal output continuously at the start of the test sequence until at least about 10 seconds after the start and the predetermined threshold may include any value from about 10 to about 30; the calculating step may include utilizing an equation of the form:

$$GT_0 = \left[\frac{I_T - \text{Intercept}}{\text{Slope}}\right]$$

where $G_0$ represents an analyte concentration;

$I_T$ represents a signal measured at a specified sampling time Tss;

Slope represents the value obtained from calibration testing of a batch of test strips of which this particular strip comes from; and Intercept represents the value obtained from calibration testing of a batch of test strips of which this particular strip comes from.

In the aforementioned aspects of the disclosure, the steps of determining, estimating, calculating, computing, deriving and/or utilizing (possibly in conjunction with an equation) may be performed by an electronic circuit or a processor. These steps may also be implemented as executable instructions stored on a computer readable medium; the instructions, when executed by a computer may perform the steps of any one of the aforementioned methods.

In additional aspects of the disclosure, there are computer readable media, each medium comprising executable instructions, which, when executed by a computer, perform the steps of any one of the aforementioned methods.

In additional aspects of the disclosure, there are devices, such as test meters or analyte testing devices, each device or meter comprising an electronic circuit or processor configured to perform the steps of any one of the aforementioned methods.

These and other embodiments, features and advantages will become apparent to those skilled in the art when taken with reference to the following more detailed description of the exemplary embodiments of the invention in conjunction with the accompanying drawings that are first briefly described.

BRIEF DESCRIPTION OF THE DRAWINGS

The accompanying drawings, which are incorporated herein and constitute part of this specification, illustrate presently preferred embodiments of the invention, and, together with the general description given above and the detailed description given below, serve to explain features of the invention (wherein like numerals represent like elements), in which:

FIG. 3A(2) illustrates a variation of the test strip of FIG. 3A(1) in which a shielding or grounding electrode is provided for proximate the entrance of the test chamber;

FIG. 3A(3) illustrates a variation of the test strip of FIG. 3A(2) in which a reagent area has been extended upstream to cover at least one of the physical characteristic sensing electrodes;

FIG. 3A(4) illustrates a variation of test strip 100 of FIGS. 3A(1), 3A(2) and 3A(3) in which certain components of the test strip have been integrated together into a single unit;

FIGS. 3C and 3D illustrate variations of FIG. 3A(1), 3A(2), or 3A(3) in which the physical characteristic sensing electrodes are disposed next to each other at the terminal end of the test chamber with the measurement electrodes upstream of the physical characteristic sensing electrodes.

FIGS. 3E and 3F illustrates physical characteristic sensing electrodes arrangement similar to that of FIG. 3A(1), 3A(2), or 3A(3) in which the pair of physical characteristic sensing electrodes are proximate the entrance of the test chamber.

FIG. 4C illustrates normal output transients and anomalous output transients from respective first and second working electrodes;

MODES OF CARRYING OUT THE INVENTION

The following detailed description should be read with reference to the drawings, in which like elements in different drawings are identically numbered. The drawings, which are not necessarily to scale, depict selected embodiments and are not intended to limit the scope of the invention. The detailed description illustrates by way of example, not by way of limitation, the principles of the invention. This description will clearly enable one skilled in the art to make and use the invention, and describes several embodiments, adaptations, variations, alternatives and uses of the invention, including what is presently believed to be the best mode of carrying out the invention.

As used herein, the terms "about" or "approximately" for any numerical values or ranges indicate a suitable dimensional tolerance that allows the part or collection of components to function for its intended purpose as described herein. More specifically, "about" or "approximately" may refer to the range of values ±10% of the recited value, e.g. "about 90%" may refer to the range of values from 81% to 99%. In addition, as used herein, the terms "patient," "host," "user," and "subject" refer to any human or animal subject and are not intended to limit the systems or methods to human use, although use of the subject invention in a human patient represents a preferred embodiment. As used herein, "oscillating signal" includes voltage signal(s) or current signal(s) that, respectively, change polarity or alternate direction of current or are multi-directional. Also used herein, the phrase "electrical signal" or "signal" is intended to include direct current signal, alternating signal or any signal within the electromagnetic spectrum. The terms "processor"; "microprocessor"; or "microcontroller" are intended to have the same meaning and are intended to be used interchangeably. As used herein, the term "annunciated" and variations on its root term indicate that an announcement may be provided via text, audio, visual or a combination of all modes or mediums of communication to a user.

Figure 1A:
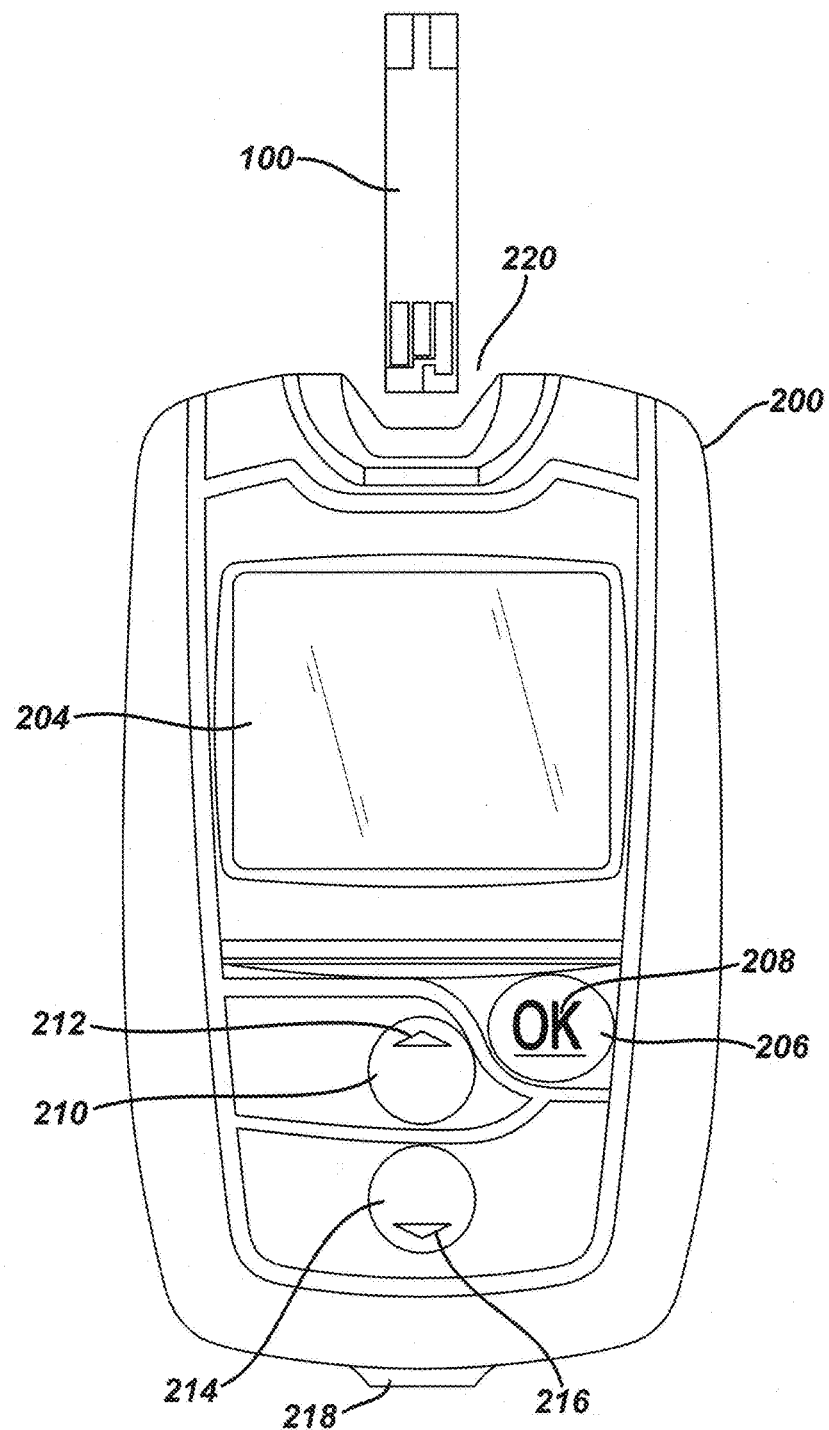
FIG. 1A illustrates an analyte measurement system including a meter and a biosensor.

FIG. 1A illustrates a test meter 200 for testing analyte (e.g., glucose) levels in the blood of an individual with a biosensor produced by the methods and techniques illustrated and described herein. Test meter 200 may include user interface inputs (206, 210, 214), which can be in the form of buttons, for entry of data, navigation of menus, and execution of commands. Data can include values representative of analyte concentration, and/or information that are related to the everyday lifestyle of an individual. Information, which is related to the everyday lifestyle, can include food intake, medication use, the occurrence of health check-ups, general health condition and exercise levels of an individual. Test meter 200 can also include a display 204 that can be used to report measured glucose levels, and to facilitate entry of lifestyle related information.

Test meter 200 may include a first user interface input 206, a second user interface input 210, and a third user interface input 214. User interface inputs 206, 210, and 214 facilitate entry and analysis of data stored in the testing device, enabling a user to navigate through the user interface displayed on display 204. User interface inputs 206, 210, and 214 include a first marking 208, a second marking 212, and a third marking 216, which help in correlating user interface inputs to characters on display 204.

Test meter 200 can be turned on by inserting a biosensor 100 (or its variants) into a strip port connector 220, by pressing and briefly holding first user interface input 206, or by the detection of data traffic across a data port 218. Test meter 200 can be switched off by removing biosensor 100 (or its variants), pressing and briefly holding first user interface input 206, navigating to and selecting a meter off option from a main menu screen, or by not pressing any buttons for a predetermined time. Display 204 can optionally include a backlight.

In one embodiment, test meter 200 can be configured to not receive a calibration input for example, from any external source, when switching from a first test strip batch to a second test strip batch. Thus, in one exemplary embodiment, the meter is configured to not receive a calibration input from external sources, such as a user interface (such as inputs 206, 210, 214), an inserted test strip, a separate code key or a code strip, data port 218. Such a calibration input is not necessary when all of the biosensor batches have a substantially uniform calibration characteristic. The calibration input can be a set of values ascribed to a particular biosensor batch. For example, the calibration input can include a batch "slope" value and a batch "intercept" value for a particular biosensor batch. The calibrations input, such as batch slope and intercept values, may be preset within the meter as will be described below.

Figure 2A:
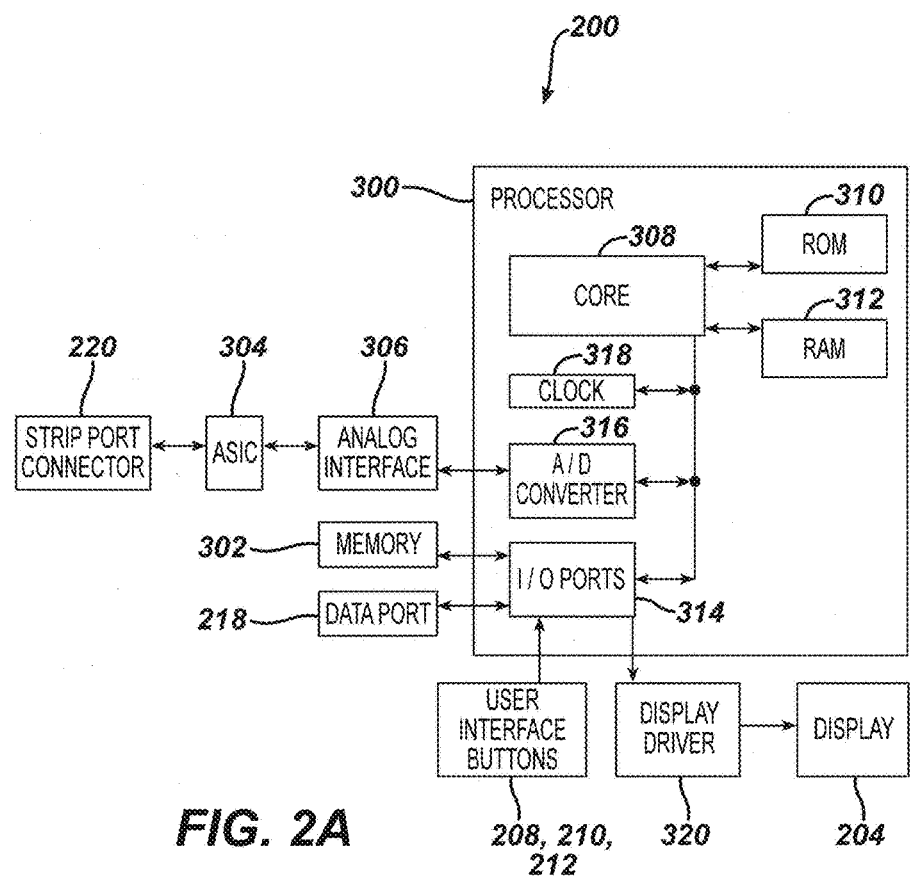
FIG. 2A illustrates in simplified schematic form the components of the meter 200.

Referring to FIG. 2A, an exemplary internal layout of test meter 200 is shown. Test meter 200 may include a processor 300, which in some embodiments described and illustrated herein is a 32-bit RISC microcontroller. In the preferred embodiments described and illustrated herein, processor 300 is preferably selected from the MSP 430 family of ultra-low power microcontrollers manufactured by Texas Instruments of Dallas, Tex. The processor can be bi-directionally connected via I/O ports 314 to a memory 302, which in some embodiments described and illustrated herein is an EEPROM. Also connected to processor 300 via I/O ports 214 are the data port 218, the user interface inputs 206, 210, and 214, and a display driver 320. Data port 218 can be connected to processor 300, thereby enabling transfer of data between memory 302 and an external device, such as a personal computer. User interface inputs 206, 210, and 214 are directly connected to processor 300. Processor 300 controls display 204 via display driver 320. Memory 302 may be pre-loaded with calibration information, such as batch slope and batch intercept values, during production of test meter 200. This pre-loaded calibration information can be accessed and used by processor 300 upon receiving a suitable signal (such as current) from the strip via strip port connector 220 so as to calculate a corresponding analyte level (such as blood glucose concentration) using the signal and the calibration information without receiving calibration input from any external source.

In embodiments described and illustrated herein, test meter 200 may include an Application Specific Integrated Circuit (ASIC) 304, so as to provide electronic circuitry used in measurements of glucose level in blood that has been applied to a test strip 100 (or its variants) inserted into strip port connector 220. Analog voltages can pass to and from ASIC 304 by way of an analog interface 306. Analog signals from analog interface 306 can be converted to digital signals by an A/D converter 316. Processor 300 further includes a core 308, a ROM 310 (containing computer code), a RAM 312, and a clock 318. In one embodiment, the processor 300 is configured (or programmed) to disable all of the user interface inputs except for a single input upon a display of an analyte value by the display unit such as, for example, during a time period after an analyte measurement. In an alternative embodiment, the processor 300 is configured (or programmed) to ignore any input from all of the user interface inputs except for a single input upon a display of an analyte value by the display unit. Detailed descriptions and illustrations of the meter 200 are shown and described in International Patent Application Publication No. WO2006070200, which is hereby incorporated by reference into this application as if fully set forth herein.

Figure 1B:
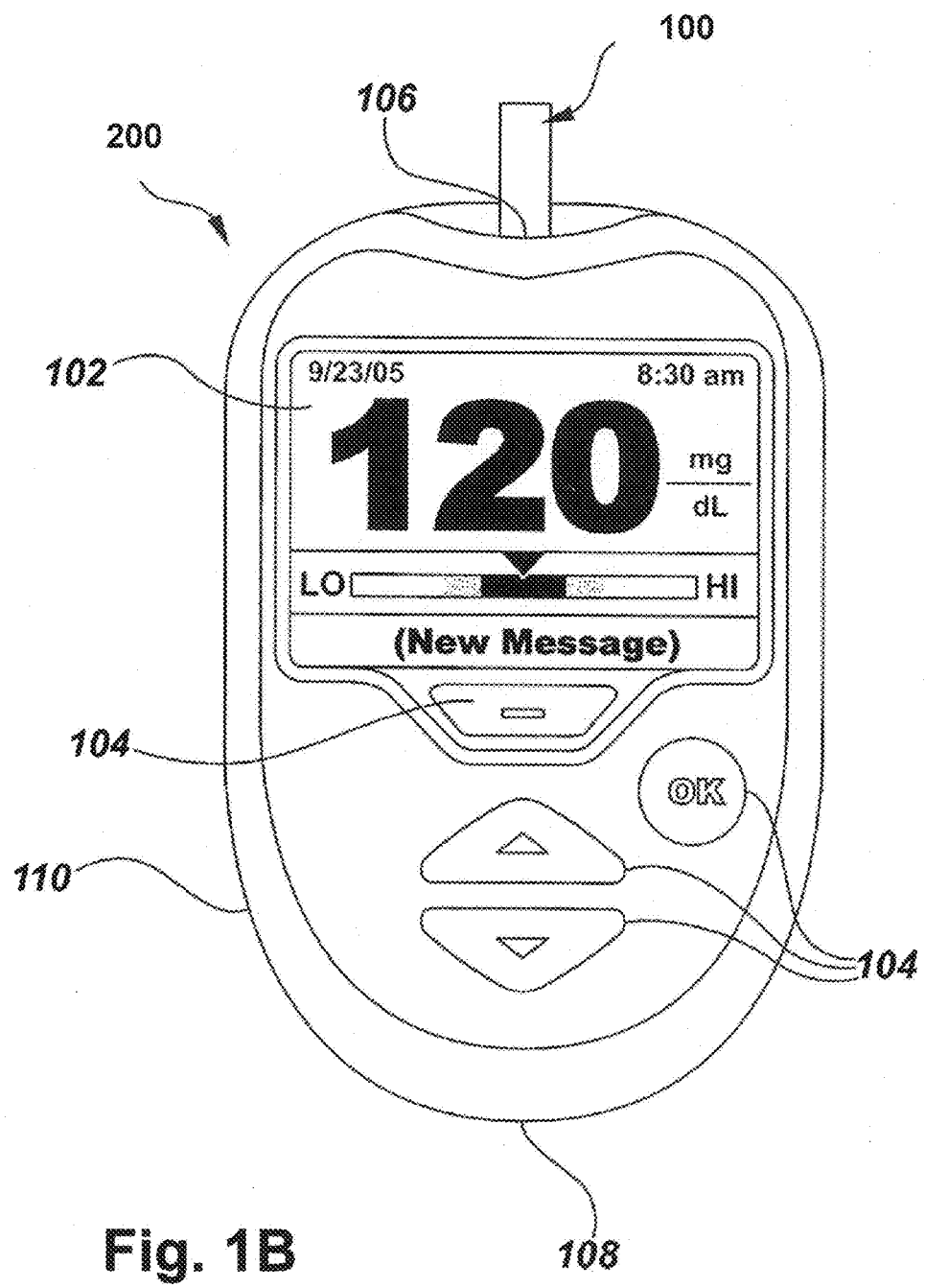
FIG. 1B illustrates yet another analyte measurement system including a meter and a biosensor.

Referring to FIGS. B and 2C through 2G, another embodiment of a hand-held test meter 200 is provided. This version of the meter 200 includes a display 102, a plurality of user interface buttons 104, a strip port connector 106, a USB interface 108, and a housing. Referring to FIGS. 1B and 2C in particular, hand-held test meter 200 also includes a microcontroller block 112, a physical characteristic measurement block 114, a display control block 116, a memory block 118 and other electronic components (not shown) for applying a test voltage to biosensor, and also for measuring an electrochemical response (e.g., plurality of test current values) and determining an analyte based on the electrochemical response. To simplify the current descriptions, the FIGURES do not depict all such electronic circuitry.

Display 102 can be, for example, a liquid crystal display or a bi-stable display configured to show a screen image. An example of a screen image may include a glucose concentration, a date and time, an error message, and a user interface for instructing an end user how to perform a test.

Strip port connector 106 is configured to operatively interface with a biosensor 100, such as an electrochemical-based biosensor configured for the determination of glucose in a whole blood sample. Therefore, the biosensor is configured for operative insertion into strip port connector 106 and to operatively interface with phase-shift-based hematocrit measurement block 114 via, for example, suitable electrical contacts.

USB Interface 108 can be any suitable interface known to one skilled in the art. USB Interface 108 is essentially a passive component that is configured to power and provide a data line to hand-held test meter 200.

Once a biosensor is interfaced with hand-held test meter 200, or prior thereto, a bodily fluid sample (e.g., a whole blood sample) is introduced into a sample chamber of the biosensor. The biosensor can include enzymatic reagents that selectively and quantitatively transform an analyte into another predetermined chemical form. For example, the biosensor can include an enzymatic reagent with ferricyanide and glucose oxidase so that glucose can be physically transformed into an oxidized form.

Memory block 118 of hand-held test meter 200 includes a suitable algorithm and can be configured, along with microcontroller block 112 to determine an analyte based on the electrochemical response of biosensor and the hematocrit of the introduced sample. For example, in the determination of the analyte blood glucose, the hematocrit can be used to compensate for the effect of hematocrit on electrochemically determined blood glucose concentrations.

Microcontroller block 112 is disposed within housing and can include any suitable microcontroller and/or micro-processor known to those of skill in the art. One such suitable microcontroller is a microcontroller commercially available from Texas Instruments, Dallas, Tex. USA and part number MSP430F5138. This microcontroller can generate a square wave of 25 to 250 kHz and a 90 degree phase-shifted wave of the same frequency and, thereby, function as a signal generation s-block described further below. MSP430F5138 also has Analog-to-Digital (A/D) processing capabilities suitable for measuring voltages generated by phase shift based hematocrit measurement blocks employed in embodiments of the present disclosure.

Figure 2B:
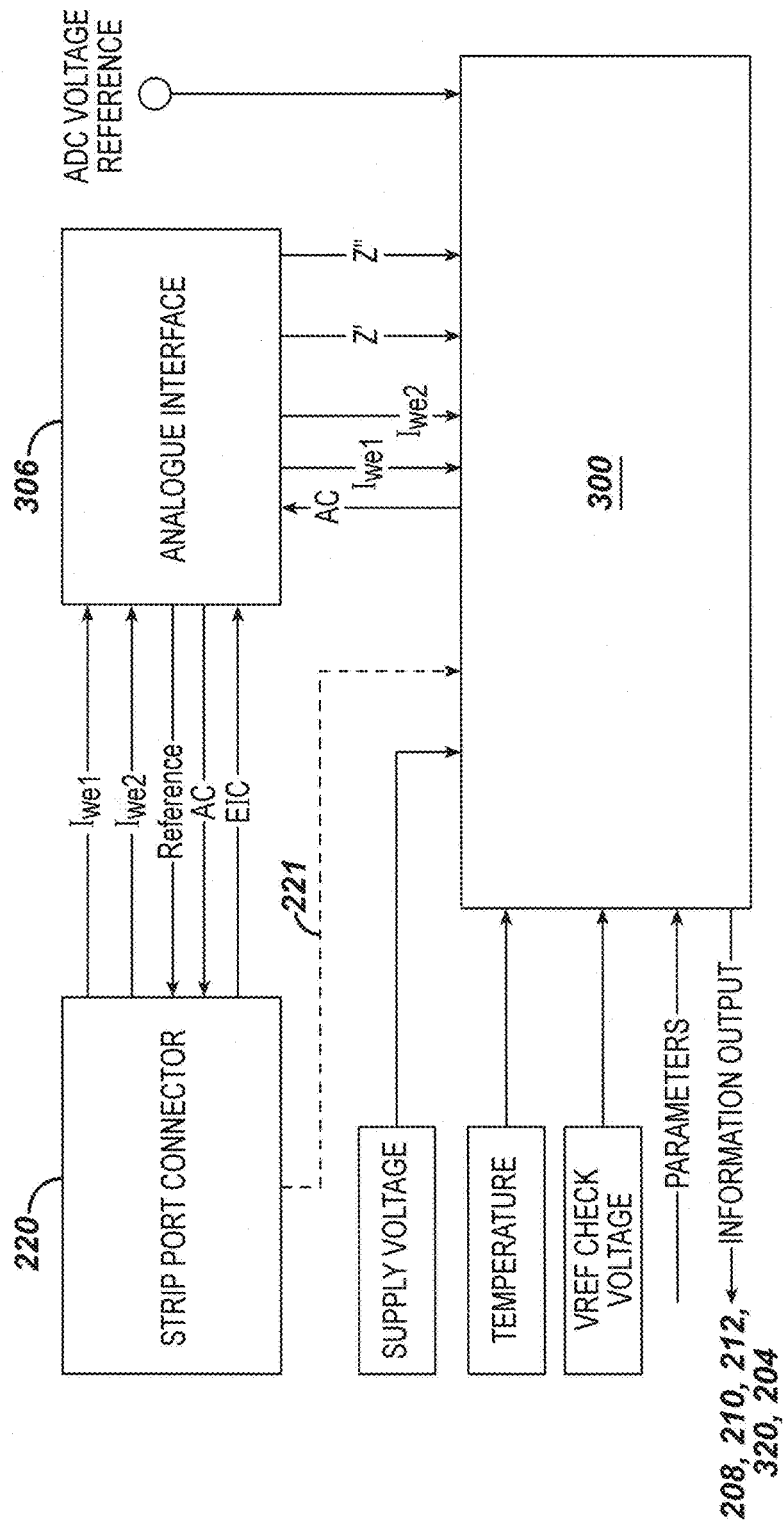
FIG. 2B illustrates in simplified schematic form a preferred implementation of a variation of meter 200.
Figure 2C:
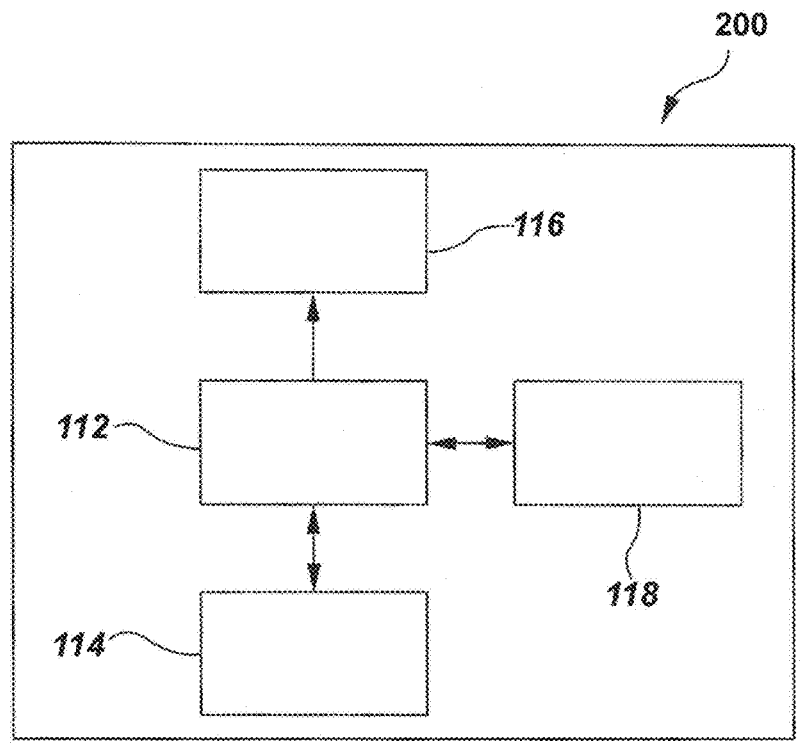
FIG. 2C is a simplified block diagram of various blocks of the hand-held test meter of FIGS. 1A and 1B.
Figure 2D:
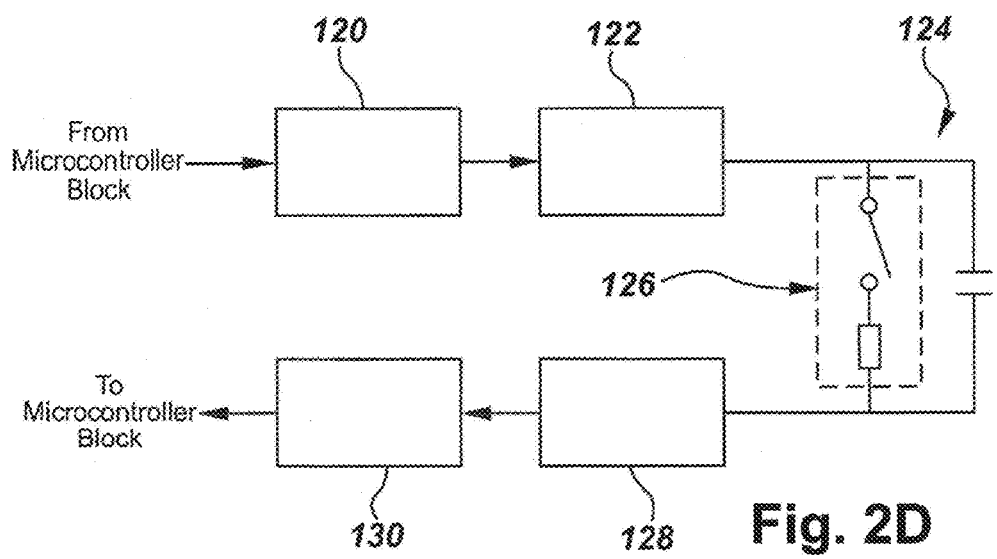
FIG. 2D is a simplified block diagram of a physical characteristic measurement block as can be employed in embodiments according to the present disclosure.

Referring in particular to FIGS. 2C and 2D, phase-shift-based hematocrit measurement block 114 (in FIG. 2C) includes a signal generation sub-block 120, a low pass filter sub-block 122, an biosensor sample cell interface sub-block 124, an optional calibration load block 126 (within the dashed lines of FIG. 2D), a transimpedance amplifier sub-block 128, and a phase detector sub-block 130.

As described further below, phase-shift-based hematocrit measurement block 114 and microcontroller block 112 are configured to measure the phase shift of a bodily fluid sample in a sample cell of an biosensor inserted in the hand-held test meter by, for example, measuring the phase shift of one or more high frequency electrical signals driven through the bodily fluid sample. In addition, microcontroller block 112 is configured to compute the hematocrit of the bodily fluid based on the measured phase shift. Microcontroller 112 can compute the hematocrit by, for example, employing an A/D converter to measure voltages received from a phase-detector sub-block, convert the voltages into a phase-shift and then employing a suitable algorithm or look-up table to convert the phase-shift into a hematocrit value. Once apprised of the present disclosure, one skilled in the art will recognize that such an algorithm and/or look-up table will be configured to take into account various factors such as strip geometry (including electrode area and sample chamber volume) and signal frequency.

It has been determined that a relationship exists between the reactance of a whole blood sample and the hematocrit of that sample. Electrical modeling of a bodily fluid sample (i.e., a whole blood sample) as parallel capacitive and resistive components indicates that when an alternating current (AC) signal is forced through the bodily fluid sample, the phase shift of the AC signal will be dependent on both the frequency of the AC voltage and the hematocrit of the sample. Moreover, modeling indicates that hematocrit has a relatively minor effect on the phase shift when the frequency of the signal is in the range of approximately 10 kHz to 25 kHz and a maximum effect on the phase shift when the frequency of the signal is in the range of approximately 250 kHz to 500 KHz. Therefore, the hematocrit of a bodily fluid sample can be measured by, for example, driving AC signals of known frequency through the bodily fluid sample and detecting their phase shift. For example, the phase-shift of a signal with a frequency in the range of 10 kHz to 25 kHz can be used as a reference reading in such a hematocrit measurement while the phase shift of a signal with a frequency in the range of 250 kHz to 500 kHz can be used as the primary measurement.

Referring to FIGS. 2C-2G, in particular, signal generation sub-block 120 can be any suitable signal generation block and is configured to generate a square wave (0V to Vref) of a desired frequency. Such a signal generation sub-block can, if desired, be integrated into microcontroller block 112.

Figure 2E:
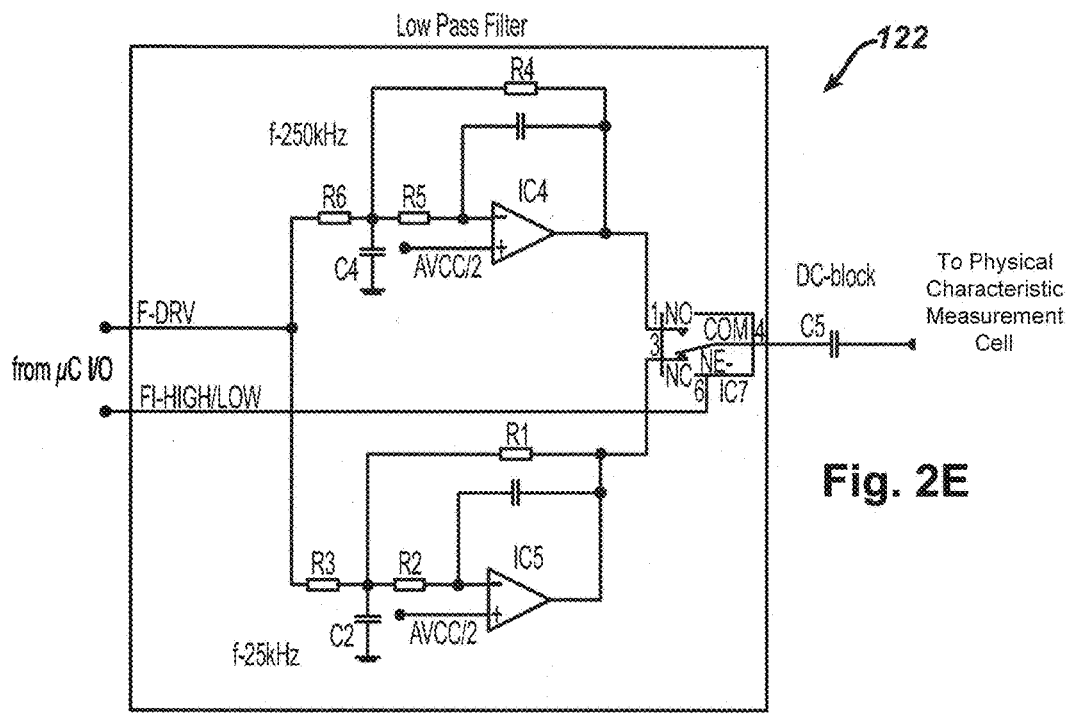
FIG. 2E is a simplified annotated schematic diagram of a dual low pass filter sub-block as can be employed in embodiments of the present disclosure.

The signal generated by signal generation sub-block 120 is communicated to dual low pass filter sub-block 122, which is configured to convert the square wave signal to a sine wave signal of a predetermined frequency. The dual LPF of FIG. 2E is configured to provide both a signal of a first frequency (such as a frequency in the range of 10 kHz to 25 kHz) and a signal of a second frequency (such as a frequency in the range of 250 kHz to 500 kHz) to the biosensor sample cell interface sub-block and an biosensors' sample chamber (also referred to as the HCT measurement cell). Selection of the first and second frequency is accomplished using switch IC7 of FIG. 2E. The dual LPF of FIG. 2E includes employs two suitable operational amplifiers (IC4 and IC5) such as the operational amplifier available from Texas Instruments, Dallas, Tex., USA as high-speed, voltage feedback, CMOS operational amplifier part number OPA354.

Referring to FIG. 2E, F-DRV represents a square wave input of either a low or high frequency (e.g., 25 kHz or 250 kHz) and is connected to both IC4 and IC5. Signal Fi-HIGH/LOW (from the microcontroller) selects the output of dual low pass filter sub-block 122 via switch IC7. C5 in FIG. 2E is configured to block the operating voltage of dual low pass filter sub-block 122 from the HCT measurement cell.

Although a specific dual LPF is depicted in FIG. 2E, dual low pass filter sub-block 122 can be any suitable low pass filter sub-block known to one skilled in the art including, for example, any suitable multiple feedback low pass filter, or a Sallen and Key low pass filter.

Figure 2F:
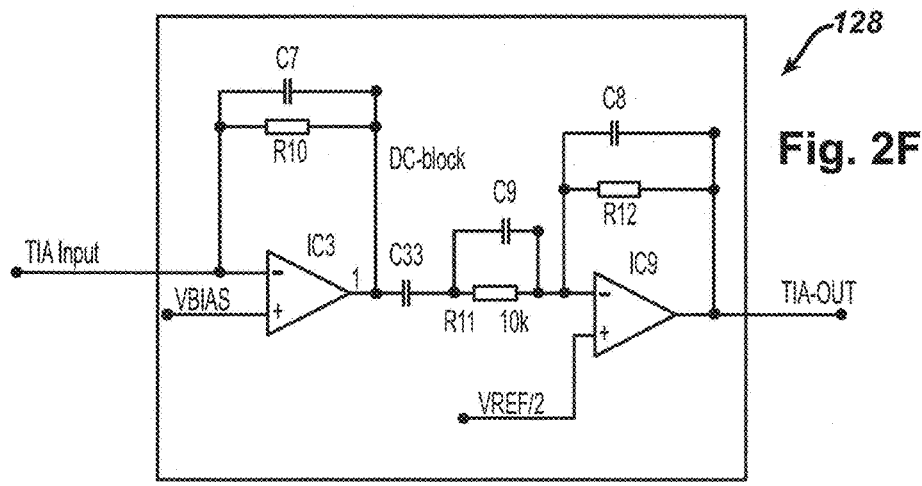
FIG. 2F is a simplified annotated schematic diagram of a transimpedance amplifier (TIA) sub-block as can be employed in embodiments of the present disclosure.
Figure 2G:
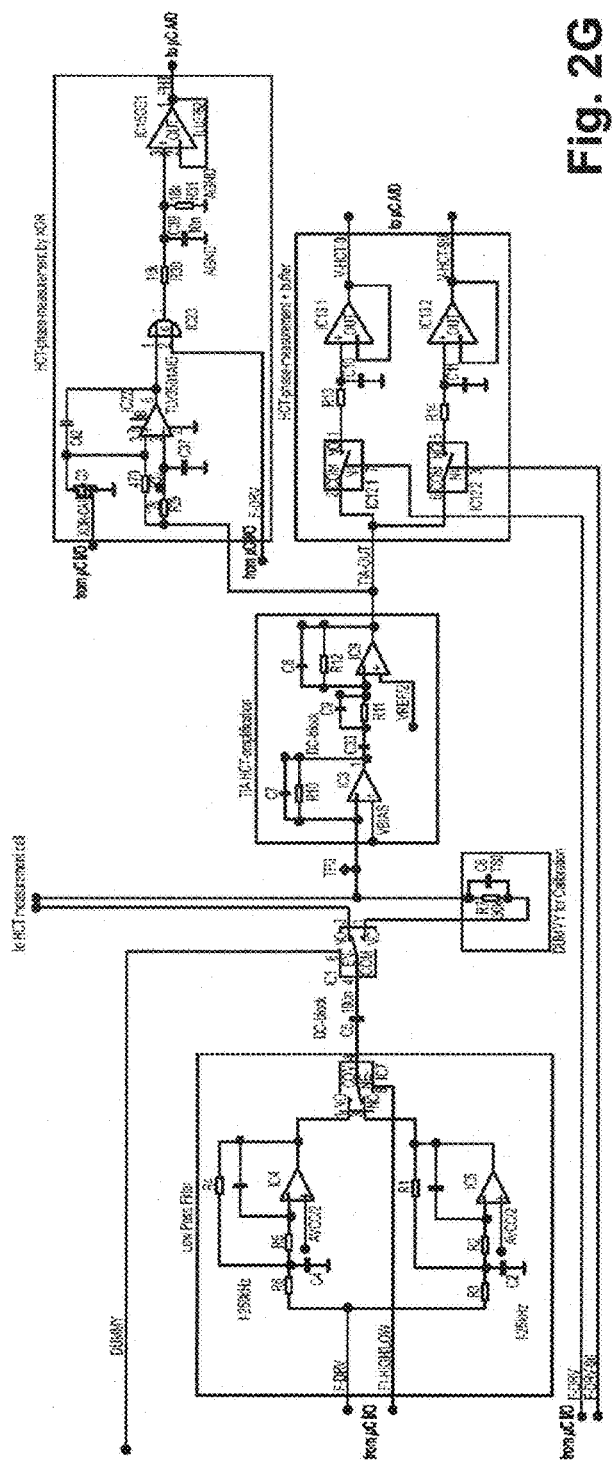
FIG. 2G is a simplified annotated schematic block diagram depicting a dual low pass filter sub-block, a calibration load sub-block, an biosensor sample cell interface sub-block, a transimpedance amplifier sub-block, an XOR phase shift measurement sub-block and a Quadratur DEMUX phase-shift measurement sub-block as can be employed in a physical characteristic measurement block of embodiments of the present disclosure FIG. 3A(1) illustrates the test strip 100 of the system of FIG. 1 in which there are two physical characteristic sensing electrodes upstream of the measurement electrodes.

The sine wave produced by low pass filter sub-block 122 is communicated to biosensor sample cell interface sub-block 124 where it is driven across the sample cell of the biosensor (also referred to as an HCT measurement cell). Biosensor sample cell interface block 124 can be any suitable sample cell interface block including, for example, an interface block configured to operatively interface with the sample cell of the biosensor via first electrode and second electrodes of the biosensor disposed in the sample cell. In such a configuration, the signal can be driven into the sample cell (from the low pass filter sub-block) via the first electrode and picked-up from the sample cell (by the transimpedance amplifier sub-block) via the second electrode as depicted in FIG. 2G.

The current produced by driving the signal across the sample cell is picked-up by transimpedance amplifier sub-block 128 and converted into a voltage signal for communication to phase detector sub-block 130.

Transimpedance sub-block 128 can be any suitable transimpedance sub-block known to one skilled in the art. FIG. 2F is a simplified annotated schematic block diagram of one such transimpedance amplifier sub-block (based on two OPA354 operational amplifiers, IC3 and IC9). The first stage of TIA sub-block 128 operates at, for example, 400 mV, which limits the AC amplitude to +/−400 mV. The second stage of TIA sub-block 128 operates at Vref/2, a configuration which enables the generation of an output of the full span of the microcontroller A/D inputs. C9 of TIA sub-block 128 serves as a blocking component that only allows an AC sine wave signal to pass.

Phase detector sub-block 130 can be any suitable phase detector sub-block that produces either a digital frequency that can be read back by microcontroller block 112 using a capture function, or an analog voltage that can be read back by microcontroller block 112 using an analog to digital converter. FIG. 2G depicts a schematic that includes two such phase detector sub-blocks, namely an XOR phase detector (in the upper half of FIG. 2G and including IC22 and IC23) and a Quadrature DEMUX phase detector (in the lower half of FIG. 2G and including IC12 and IC13).

FIG. 2G also depicts a calibration load sub-block 126 that includes a switch (IC16) and a dummy load R7 and C6. Calibration load sub-block 126 is configured for the dynamic measurement of a phase offset for the known phase shift of zero degrees produced by resistor R7, thus providing a phase offset for use in calibration. C6 is configured to force a predetermined slight phase shift, e.g. to compensate for phase delays caused by parasitic capacities in the signal traces to the sample cell, or for phase delays in the electrical circuits (LPF and TIA).

The Quadrature DEMUX phase detector circuit of FIG. 2G includes two portions, one portion for a resistive part of the incoming AC signal and one portion for the reactive portion of the incoming AC signal. Use of such two portions enables the simultaneous measurement of both the resistive and reactive portion of the AC signal and a measurement range that covers 0 degrees to 360 degrees. The Quadrature DEMUX circuit of FIG. 2G generates two separate output voltages. One of these output voltages represents the "in phase measurement" and is proportional to the "resistive" part of the AC signal, the other output voltage represents the "Quadrature Measurement" and is proportional to the "reactive part of the signal. The phase shift is calculated as:

$$\Phi = \tan^{-1}(V_{QUAD\text{-}PHASE}/V_{IN\text{-}PHASE})$$

Such a Quadrature DEMUX phase detector circuit can also be employed to measure the impedance of a bodily fluid sample in the sample cell. It is hypothesized, without being bound, that the impedance could be employed along with the phase-shift, or independently thereof, to determine the hematocrit of the bodily sample. The amplitude of a signal forced through the sample cell can be calculated using the two voltage outputs of the Quadrature DEMUX circuit as follows:

$$\text{Amplitude} = \text{SQR}((V_{QUAD\text{-}PHASE})^2 + (V_{IN\text{-}PHASE})^2)$$

This amplitude can then be compared to an amplitude measured for the known resistor of calibration load block 126 to determine the impedance.

The XOR phase detector portion has a measurement range of 0° to 180°, or alternatively a measurement range of −90° to +90°, depending whether the "Square wave input from μC" is in phase to the sine wave or is set to a 90° phase shift. The XOR phase detector produces an output frequency that is always double the input frequency, however the duty cycle varies. If both inputs are perfectly in phase, the output is LOW, if both inputs are 180° shifted the output is always HIGH. By integrating the output signal (e.g. via a simple RC element) a voltage can be generated that is directly proportional to the phase shift between both inputs.

As provided herein, one skilled in the art will recognize that phase detector sub-blocks employed in embodiments of the present disclosure can take any suitable form and include, for example, forms that employ rising edge capture techniques, dual edge capture techniques, XOR techniques and synchronous demodulation techniques.

Since low pass filter sub-block 122, transimpedance amplifier sub-block 128 and phase detector sub-block 130 can introduce a residual phase shift into phase-shift-based hematocrit measurement block 114, calibration load block 126 can be optionally included in the phase-shift-based hematocrit measurement block. Calibration load block 126 is configured to be essentially resistive in nature (for example a 33 k-ohm load) and, therefore, induces no phase shift between excitation voltage and generated current. Calibration load block 126 is configured to be switched in across the circuit to give a "zero" calibration reading. Once calibrated, the hand-held test meter can measure the phase shift of a bodily fluid sample, subtract the "zero" reading to compute a corrected phase shift and subsequently compute the physical characteristic of the sample based on the corrected phase shift.

FIG. 3A(1) is an exemplary exploded perspective view of a test strip 100, which may include seven layers disposed on a substrate 5. The seven layers disposed on substrate 5 can be a first conductive layer 50 (which can also be referred to as electrode layer 50), an insulation layer 16, two overlapping reagent layers 22a and 22b, an adhesive layer 60 which includes adhesive portions 24, 26, and 28, a hydrophilic layer 70, and a top layer 80 which forms a cover 94 for the test strip 100. Test strip 100 may be manufactured in a series of steps where the conductive layer 50, insulation layer 16, reagent layers 22a and 22b, and adhesive layer 60 are sequentially deposited on substrate 5 using, for example, a screen-printing process. Note that the electrodes 10, 12, and 14) are disposed for contact with the reagent layers 22a and 22b whereas the physical characteristic sensing electrodes 19a and 20a are spaced apart and not in contact with the reagent layers 22a and 22b. Hydrophilic layer 70 and top layer 80 can be disposed from a roll stock and laminated onto substrate 5 as either an integrated laminate or as separate layers. Test strip 100 has a distal portion 3 and a proximal portion 4 as shown in FIG. 3A(1).

Test strip 100 may include a sample-receiving chamber 92 through which a physiological fluid sample 95 may be drawn through or deposited (FIG. 3A(2)). The physiological fluid sample discussed herein may be blood. Sample-receiving chamber 92 can include an inlet at a proximal end and an outlet at the side edges of test strip 100, as illustrated in FIG. 3A(1). A fluid sample 95 can be applied to the inlet along axis L-L (FIG. 3A(2)) to fill a sample-receiving chamber 92 so that glucose can be measured. The side edges of a first adhesive pad 24 and a second adhesive pad 26 located adjacent to reagent layer 22 (which may include 22a and 22b) each define a wall of sample-receiving chamber 92, as illustrated in FIG. 3A(1). A bottom portion or "floor" of sample-receiving chamber 92 may include a portion of substrate 5, conductive layer 50, and insulation layer 16, as illustrated in FIG. 3A(1). A top portion or "roof" of sample-receiving chamber 92 may include distal hydrophilic portion 32, as illustrated in FIG. 3A(1). For test strip 100, as illustrated in FIG. 3A(1), substrate 5 can be used as a foundation for helping support subsequently applied layers. Substrate 5 can be in the form of a polyester sheet such as a polyethylene tetraphthalate (PET) material (Hostaphan PET supplied by Mitsubishi). Substrate 5 can be in a roll format, nominally 350 microns thick by 370 millimeters wide and approximately 60 meters in length.

A conductive layer is required for forming electrodes that can be used for the electrochemical measurement of glucose. First conductive layer 50 can be made from a carbon ink that is screen-printed onto substrate 5. In a screen-printing process, carbon ink is loaded onto a screen and then transferred through the screen using a squeegee. The printed carbon ink can be dried using hot air at about 140° C. The carbon ink can include VAGH resin, carbon black, graphite (KS 15), and one or more solvents for the resin, carbon and graphite mixture. More particularly, the carbon ink may incorporate a ratio of carbon black:VAGH resin of about 2.90:1 and a ratio of graphite:carbon black of about 2.62:1 in the carbon ink.

For test strip 100, as illustrated in FIG. 3A(1), first conductive layer 50 may include a reference electrode 10, a first working electrode 12, a second working electrode 14, third and fourth physical characteristic sensing electrodes 19a and 20a, a first contact pad 13, a second contact pad 15, a reference contact pad 11, a first working electrode track 8, a second working electrode track 9, a reference electrode track 7, and a strip detection bar 17. The physical characteristic sensing electrodes 19a and 20a are provided with respective electrode tracks 19b and 20b. The conductive layer may be formed from carbon ink. First contact pad 13, second contact pad 15, and reference contact pad 11 may be adapted to electrically connect to a test meter. First working electrode track 8 provides an electrically continuous pathway from first working electrode 12 to first contact pad 13. Similarly, second working electrode track 9 provides an electrically continuous pathway from second working electrode 14 to second contact pad 15. Similarly, reference electrode track 7 provides an electrically continuous pathway from reference electrode 10 to reference contact pad 11. Strip detection bar 17 is electrically connected to reference contact pad 11. Third and fourth electrode tracks 19b and 20b connect to the respective electrodes 19a and 20a. A test meter can detect that test strip 100 has been properly inserted by measuring a continuity between reference contact pad 11 and strip detection bar 17, as illustrated in FIG. 3A(1).

Figure 3B:
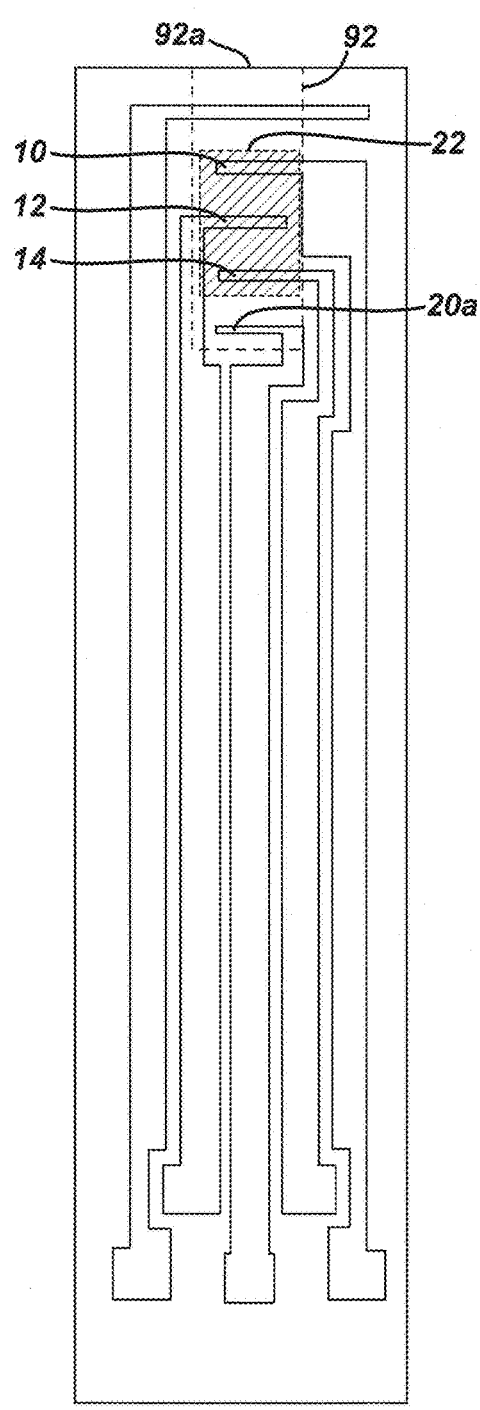
FIG. 3B illustrates a variation of the test strip of FIG. 3A(1), 3A(2), or 3A(3) in which one physical characteristic sensing electrode is disposed proximate the entrance and the other physical characteristic sensing electrode is at the terminal end of the test cell with the measurement electrodes disposed between the pair of physical characteristic sensing electrodes.
Figure 3C:
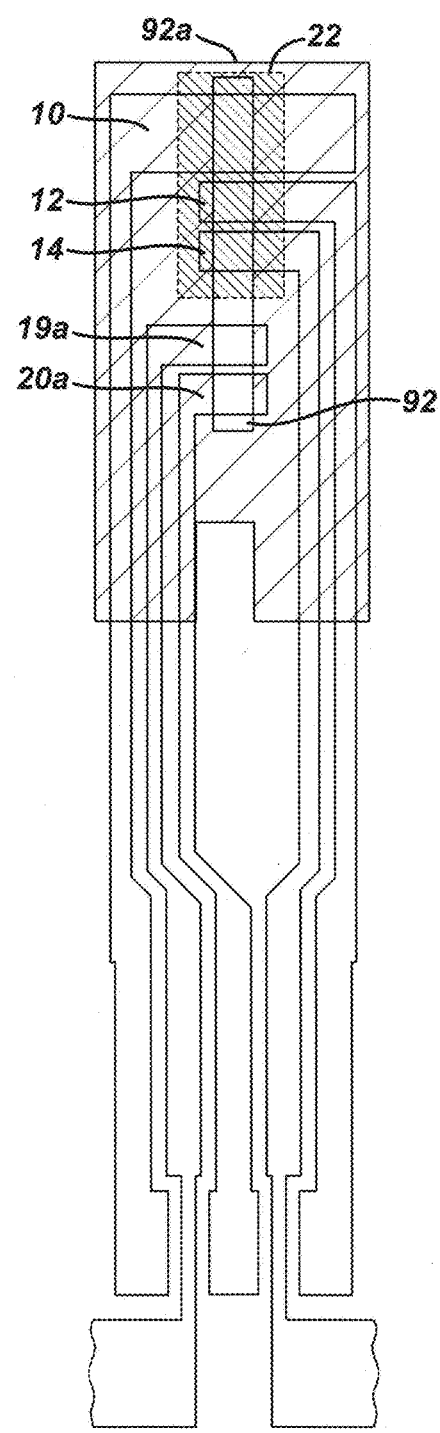

Variations of the test strip 100 (FIG. 3A(1), 3A(2), 3A(3), or 3A(4)) are shown in FIGS. 3B-3F. Briefly, with regard to variations of test strip 100, these test strips include an enzymatic reagent layer disposed on the working electrode, a patterned spacer layer disposed over the first patterned conductive layer and configured to define a sample chamber within the biosensor, and a second patterned conductive layer disposed above the first patterned conductive layer. The second patterned conductive layer includes a first phase-shift measurement electrode and a second phase-shift measurement electrode. Moreover, the first and second phase-shift measurement electrodes are disposed in the sample chamber and are configured to measure, along with the hand-held test meter, a phase shift of an electrical signal forced through a bodily fluid sample introduced into the sample chamber during use of the biosensor. Such phase-shift measurement electrodes are also referred to herein as bodily fluid phase-shift measurement electrodes. Biosensors of various embodiments described herein are believed to be advantageous in that, for example, the first and second phase-shift measurement electrodes are disposed above the working and reference electrodes, thus enabling a sample chamber of advantageously low volume. This is in contrast to a configuration wherein the first and second phase-shift measurement electrodes are disposed in a co-planar relationship with the working and reference electrodes thus requiring a larger bodily fluid sample volume and sample chamber to enable the bodily fluid sample to cover the first and second phase-shift measurement electrodes as well as the working and reference electrodes.

In the embodiment of FIG. 3A(2) which is a variation of the test strip of FIG. 3A(1), an additional electrode 10a is provided as an extension of any of the plurality of electrodes 19a, 20a, 14, 12, and 10. It must be noted that the built-in shielding or grounding electrode 10a is used to reduce or eliminate any capacitance coupling between the finger or body of the user and the characteristic measurement electrodes 19a and 20a. The grounding electrode 10a allows for any capacitance to be directed away from the sensing electrodes 19a and 20a. To do this, the grounding electrode 10a can be connected any one of the other five electrodes or to its own separate contact pad (and track) for connection to ground on the meter instead of one or more of contact pads 15, 17, 13 via respective tracks 7, 8, and 9. In a preferred embodiment, the grounding electrode 10a is connected to one of the three electrodes that has reagent 22 disposed thereon. In a most preferred embodiment, the grounding electrode 10a is connected to electrode 10. Being the grounding electrode, it is advantageous to connect the grounding electrode to the reference electrode (10) so not to contribute any additional current to the working electrode measurements which may come from background interfering compounds in the sample. Further by connecting the shield or grounding electrode 10a to electrode 10 this is believed to effectively increase the size of the counter electrode 10 which can become limiting especially at high signals. In the embodiment of FIG. 3A(2), the reagent are arranged so that they are not in contact with the measurement electrodes 19a and 20a. Alternatively, in the embodiment of FIG. 3A(3), the reagent 22 is arranged so that the reagent 22 contacts at least one of the sensing electrodes 19a and 20a.

In alternate version of test strip 100, shown here in FIG. 3A(4), the top layer 38, hydrophilic film layer 34 and spacer 29 have been combined together to form an integrated assembly for mounting to the substrate 5 with reagent layer 22' disposed proximate insulation layer 16'.

In the embodiment of FIG. 3B, the analyte measurement electrodes 10, 12, and 14 are disposed in generally the same configuration as in FIG. 3A(1), 3A(2), or 3A(3). The electrodes 19a and 20a to sense physical characteristic (e.g., hematocrit) level, however, are disposed in a spaced apart configuration in which one electrode 19a is proximate an entrance 92a to the test chamber 92 and another electrode 20a is at the opposite end of the test chamber 92. Electrodes 10, 12, and 14 are disposed to be in contact with a reagent layer 22.

Figure 3F:
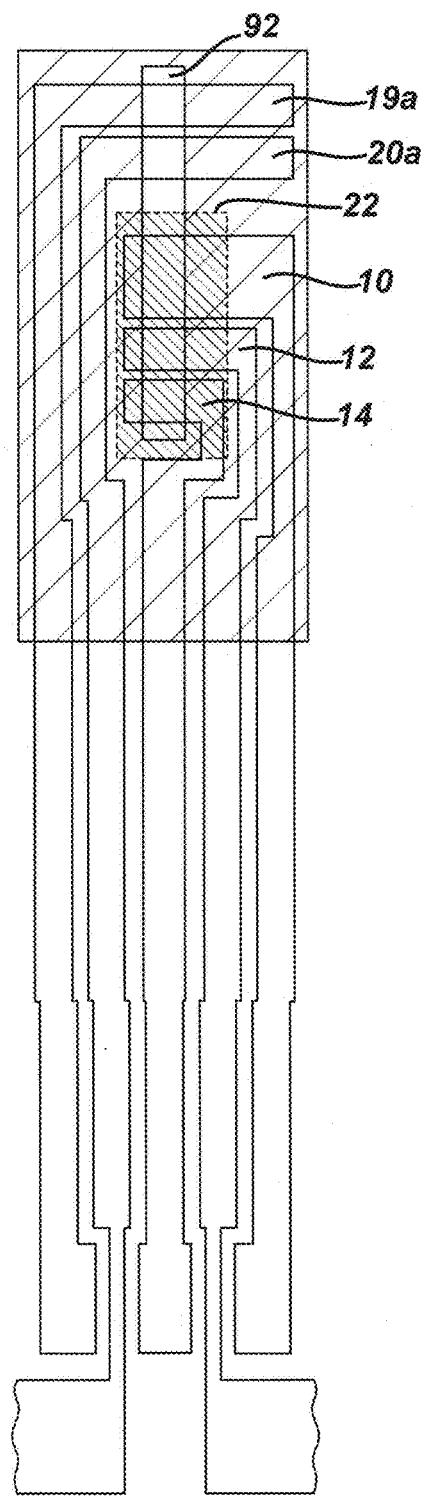

In FIGS. 3C, 3D, 3E and 3F, the physical characteristic (e.g., hematocrit) sensing electrodes 19a and 20a are disposed adjacent each other and may be placed at the opposite end of the entrance 92a to the test chamber 92 (FIGS. 3C and 3D) or adjacent the entrance 92a (FIGS. 3E and 3F). In all of these embodiments, the physical characteristic sensing electrodes are spaced apart from the reagent layer 22 so that these physical characteristic sensing electrodes are not impacted by the electrochemical reaction of the reagent in the presence of a fluid sample (e.g., blood or interstitial fluid) containing glucose.

In the various embodiments of the biosensor, there are two measurements that are made to a fluid sample deposited on the biosensor. One measurement is that of the concentration of the analyte (e.g. glucose) in the fluid sample while the other is that of physical characteristic (e.g., hematocrit) in the same sample. The measurement of the physical characteristic (e.g., hematocrit) is used to modify or correct the glucose measurement so as to remove or reduce the effect of red blood cells on the glucose measurements. Both measurements (glucose and hematocrit) can be performed in sequence, simultaneously or overlapping in duration. For example, the glucose measurement can be performed first then the physical characteristic (e.g., hematocrit); the physical characteristic (e.g., hematocrit) measurement first then the glucose measurement; both measurements at the same time; or a duration of one measurement may overlap a duration of the other measurement. Each measurement is discussed in detail as follow with respect to FIGS. 4A, 4B and 5.

Figure 4A:
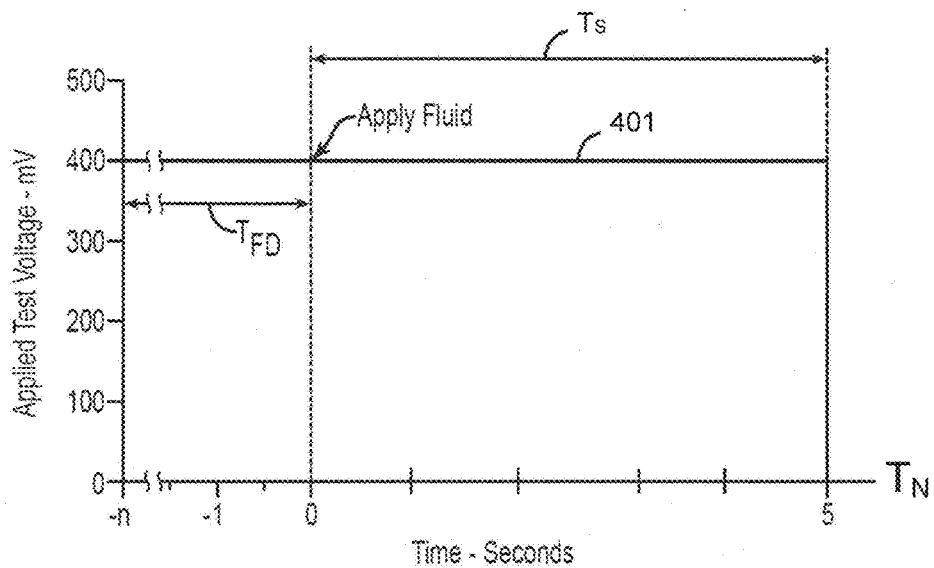
FIG. 4A illustrates a graph of time over applied potential to the biosensor of FIGS. 3A(1), 3A(2), 3A(3) and 3B-3F.

FIG. 4A is an exemplary chart of a test signal applied to test strip 100 and its variations shown herein. Before a fluid sample is applied to test strip 100 (or its variants), test meter 200 is in a fluid detection mode in which a first test signal of about 400 millivolts is applied between second working electrode and reference electrode. A second test signal of about 400 millivolts is preferably applied simultaneously between first working electrode (e.g., electrode 12 of strip 100) and reference electrode (e.g., electrode 10 of strip 100). Alternatively, the second test signal may also be applied contemporaneously such that a time interval of the application of the first test signal overlaps with a time interval in the application of the second test voltage. The test meter may be in a fluid detection mode during fluid detection time interval $T_{FD}$ prior to the detection of physiological fluid at starting time at zero. In the fluid detection mode, test meter 200 determines when a fluid is applied to test strip 100 (or its variants) such that the fluid wets either the first working electrode 12 or second working electrode 14 (or both working electrodes) with respect to reference electrode 10. Once test meter 200 recognizes that the physiological fluid has been applied because of, for example, a sufficient increase in the measured test current at either or both of first working electrode 12 and second working electrode 14, test meter 200 assigns a zero second marker at zero time "0" and starts the test time interval $T_S$. Test meter 200 may sample the current transient output at a suitable sampling rate, such as, for example, every 1 milliseconds to every 100 milliseconds. Upon the completion of the test time interval $T_S$, the test signal is removed. For simplicity, FIG. 4A only shows the first test signal applied to test strip 100 (or its variants).

Hereafter, a description of how analyte (e.g., glucose) concentration is determined from the known signal transients (e.g., the measured electrical signal response in nanoamperes as a function of time) that are measured when the test voltages of FIG. 4A are applied to the test strip 100 (or its variants).

Figure 4B:
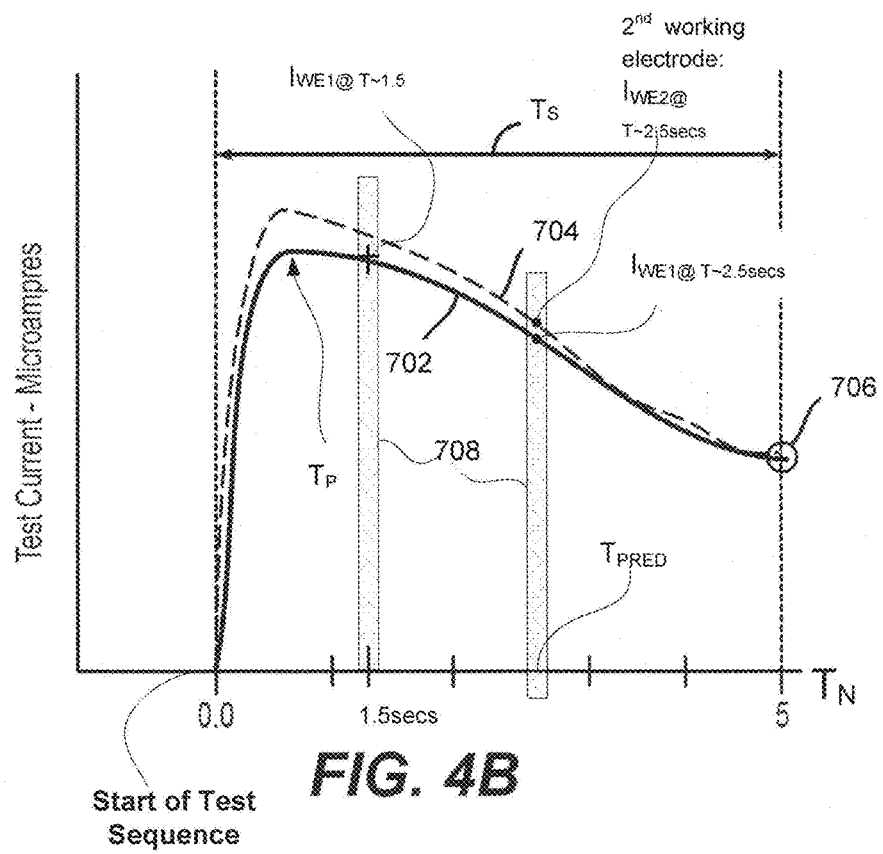
FIG. 4B illustrates a graph of time over output current from the biosensor of FIGS. 3A(1), 3A(2), 3A(3) and 3B-3F.

In FIG. 4A, the first and second test voltages applied to test strip 100 (or its variants described herein) are generally from about +100 millivolts to about +600 millivolts. In one embodiment in which the electrodes include carbon ink and the mediator includes ferricyanide, the test signal is about +400 millivolts. Other mediator and electrode material combinations will require different test voltages, as is known to those skilled in the art. The duration of the test voltages is generally from about 1 to about 5 seconds after a reaction period and is typically about 3 seconds after a reaction period. Typically, test sequence time $T_S$ is measured relative to time $t_0$. As the voltage 401 is maintained in FIG. 4A for the duration of $T_S$, output signals are generated, shown here in FIG. 4B with the current transient 702 for the first working electrode 12 being generated starting at zero time and likewise the current transient 704 for the second working electrode 14 is also generated with respect to the zero time. It is noted that while the signal transients 702 and 704 have been placed on the same referential zero point for purposes of explaining the process, in physical term, there is a slight time differential between the two signals due to fluid flow in the chamber towards each of the working electrodes 12 and 14 along axis L-L. However, the current transients are sampled and configured in the microcontroller to have the same start time. In FIG. 4B, the current transients build up to a peak proximate peak time Tp at which time, the current slowly drops off until approximately one of 2.5 seconds or 5 seconds after zero time. At the point 706, approximately at 5 seconds, the output signal for each of the working electrodes 12 and 14 may be measured and added together. Alternatively, the signal from only one of the working electrodes 12 and 14 can be doubled.

Referring back to FIG. 2B, the system drives a signal to measure or sample the output signals $I_E$ from at least one the working electrodes (12 and 14) at any one of a plurality of time points or positions $T_1, T_2, T_3, \ldots T_N$. As can be seen in FIG. 4B, the time position can be any time point or interval in the test sequence $T_S$. For example, the time position at which the output signal is measured can be a single time point $T_{1.5}$ at 1.5 seconds or an interval 708 (e.g., interval ~10 milliseconds or more depending on the sampling rate of the system) overlapping the time point $T_{2.8}$ proximate 2.8 seconds.

From knowledge of the parameters of the biosensor (e.g., batch calibration code offset and batch slope) for the particular test strip 100 and its variations, the analyte (e.g., glucose) concentration can be calculated. Output transient 702 and 704 can be sampled to derive signals $I_E$ (by summation of each of the current $I_{WE1}$ and $I_{WE2}$ or doubling of one of $I_{WE1}$ or $I_{WE2}$) at various time positions during the test sequence. From knowledge of the batch calibration code offset and batch slope for the particular test strip 100, the analyte (e.g., glucose) concentration can be calculated.

It is noted that "Intercept" and "Slope" are the values obtained by measuring calibration data from a batch of biosensors. Typically around 1500 biosensors are selected at random from the lot or batch. Physiological fluid (e.g., blood) from donors is spiked to various analyte levels, typically six different glucose concentrations. Typically, blood from 12 different donors is spiked to each of the six levels. Eight biosensors (or strips in this embodiment) are given blood from identical donors and levels so that a total of 12×6×8=576 tests are conducted for that lot. These are benchmarked against actual analyte level (e.g., blood glucose concentration) by measuring these using a standard laboratory analyzer such as Yellow Springs Instrument (YSI). A graph of measured glucose concentration is plotted against actual glucose concentration (or measured current versus YSI current) and a formula y=mx+c least squares fitted to the graph to give a value for batch slope m and batch intercept c for the remaining strips from the lot or batch. The applicants have also provided methods and systems in which the batch slope is derived during the determination of an analyte concentration. The "batch slope", or "Slope", may therefore be defined as the measured or derived gradient of the line of best fit for a graph of measured glucose concentration plotted against actual glucose concentration (or measured current versus YSI current). The "batch intercept", or "Intercept", may therefore be defined as the point at which the line of best fit for a graph of measured glucose concentration plotted against actual glucose concentration (or measured current versus YSI current) meets the y axis.

It is worthwhile here to note that the various components, systems and procedures described earlier allow for applicant to provide an analyte measurement system that heretofore was not available in the art. In particular, this system includes a biosensor that has a substrate and a plurality of electrodes connected to respective electrode connectors. The system further includes an analyte meter 200 that has a housing, a test strip port connector configured to connect to the respective electrode connectors of the test strip, and a microcontroller 300, shown here in FIG. 2B. The microcontroller 300 is in electrical communication with the test strip port connector 220 to apply electrical signals or sense electrical signals from the plurality of electrodes.

Referring to FIG. 2B, details of a preferred implementation of meter 200 where the same numerals in FIGS. 2A and 2B have a common description. In FIG. 2B, a strip port connector 220 is connected to the analogue interface 306 by five lines including an impedance sensing line EIC to receive signals from physical characteristic sensing electrode(s), alternating signal line AC driving signals to the physical characteristic sensing electrode(s), reference line for a reference electrode, and signal sensing lines from respective working electrode 1 and working electrode 2. A strip detection line 221 can also be provided for the connector 220 to indicate insertion of a test strip. The analog interface 306 provides four inputs to the processor 300: (1) real impedance Z'; (2) imaginary impedance Z"; (3) signal sampled or measured from working electrode 1 of the biosensor or $I_{we1}$; (4) signal sampled or measured from working electrode 2 of the biosensor or $I_{we2}$. There is one output from the processor 300 to the interface 306 to drive an oscillating signal AC of any value from 25 kHz to about 250 kHz or higher to the physical characteristic sensing electrodes. A phase differential P (in degrees) can be determined from the real impedance Z' and imaginary impedance Z" where:

$$P = \tan^{-1}\{Z''/Z'\} \qquad \text{Eq. 3.1}$$

and magnitude M (in ohms and conventionally written as |Z|) from line Z' and Z" of the interface 306 can be determined where $$M = \sqrt{(Z')^2 + (Z'')^2} \qquad \text{Eq. 3.2}$$

In this system, the microprocessor is configured to: (a) apply a first signal to the plurality of electrodes so that a batch slope defined by a physical characteristic of a fluid sample is derived and (b) apply a second signal to the plurality of electrodes so that an analyte concentration is determined based on the derived batch slope. For this system, the plurality of electrodes of the test strip or biosensor includes at least two electrodes to measure the physical characteristic and at least two other electrodes to measure the analyte concentration. For example, the third and fourth electrodes and the at least two other electrodes are disposed in the same chamber provided on the substrate. Alternatively, the third and fourth electrodes and the at least two other electrodes are disposed in respective two different chambers provided on the substrate. It is noted that for some embodiments, all of the electrodes are disposed on the same plane defined by the substrate. In particular, in some of the embodiments described herein, a reagent is disposed proximate the at least two other electrodes and no reagent is disposed on the third and fourth electrodes. One feature of note in this system is the ability to provide for an accurate analyte measurement within about 10 seconds of deposition of a fluid sample (which may be a physiological sample) onto the biosensor as part of the test sequence.

As an example of an analyte calculation (e.g., glucose) for strip 100 (FIG. 3A(1), 3A(2), or 3A(3)) and its variants herein, it is assumed in FIG. 4B that the sampled signal value at 706 for the first working electrode 12 is about 1600 nanoamperes whereas the signal value at 706 for the second working electrode 14 is about 1300 nanoamperes and the calibration code of the test strip indicates that the Intercept is about 500 nanoamperes and the Slope is about 18 nanoamperes/mg/dL. Glucose concentration $G_0$ can be thereafter be determined from Equation 3.3 as follow:

$$G_0 = [(I_E) - \text{Intercept}]/\text{Slope} \quad\quad \text{Eq. 3.3}$$

where $I_E$ is a signal (proportional to analyte concentration) which is the total signal from all of the electrodes in the biosensor (e.g., for sensor 100, both electrodes 12 and 14 (or $I_{we1} + I_{we2}$));

$I_{we1}$ is the signal measured for the first working electrode at the set sampling time;

$I_{we2}$ is the signal measured for the second working electrode at the set sampling time;

Slope is the value obtained from calibration testing of a batch of test strips of which this particular strip comes from;

Intercept is the value obtained from calibration testing of a batch of test strips of which this particular strip comes from.

From Eq. 3.3; $G_0 = [(1600+1300)-500]/18$ and therefore, $G_0 = 133.33$ nanoamp ~133 mg/dL.

It is noted here that although the examples have been given in relation to a biosensor 100 which has two working electrodes (12 and 14 in FIG. 3A(1)) such that the measured currents from respective working electrodes have been added together to provide for a total measured current $I_E$, the signal resulting from only one of the two working electrodes can be multiplied by two in a variation of test strip 100 where there is only one working electrode (either electrode 12 or 14). Instead of a total signal, an average of the signal from each working electrode can be used as the total measured current $I_E$ for Equations 3.3, 6, and 5-7 described herein, and of course, with appropriate modification to the operational coefficients (as known to those skilled in the art) to account for a lower total measured current $I_E$ than as compared to an embodiment where the measured signals are added together. Alternatively, the average of the measured signals can be multiplied by two and used as $I_E$ in Equations 3.3, 6, and 5-7 without the necessity of deriving the operational coefficients as in the prior example. It is noted that the analyte (e.g., glucose) concentration here is not corrected for any physical characteristic (e.g., hematocrit value) and that certain offsets may be provided to the signal values $I_{we1}$ and $I_{we2}$ to account for errors or delay time in the electrical circuit of the meter 200. Temperature compensation can also be utilized to ensure that the results are calibrated to a referential temperature such as for example room temperature of about 20 degrees Celsius.

Figure 5:
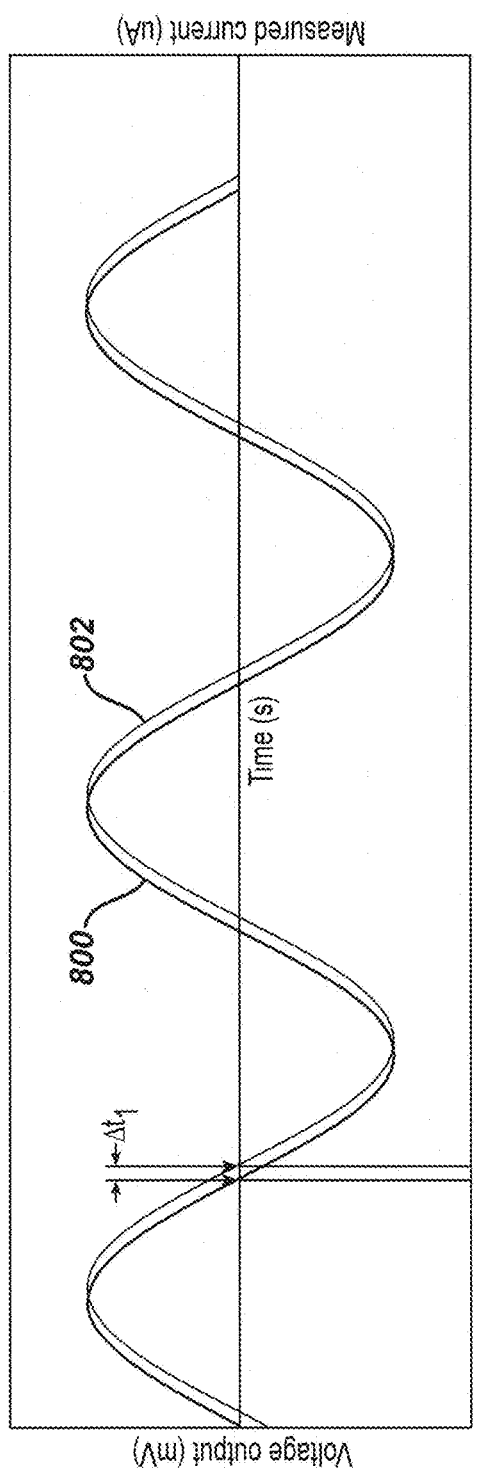
FIG. 5 illustrates an exemplary waveform applied to the test chamber and a waveform as measured from the test chamber to show a time delay between the waveforms.

Now that an analyte (e.g., glucose) concentration $(G_0)$ can be determined from the signal $I_E$, a description of applicant's technique to determine the physical characteristic (e.g., hematocrit) of the fluid sample is provided in relation to FIG. 5. In FIG. 5, the system 200 (FIG. 2) applies a first oscillating input signal 800 at a first frequency (e.g., of about 25 kilo-Hertz) to a pair of sensing electrodes. The system is also set up to measure or detect a first oscillating output signal 802 from the third and fourth electrodes, which in particular involve measuring a first time differential $\Delta t_1$ between the first input and output oscillating signals. At the same time or during overlapping time durations, the system may also apply a second oscillating input signal (not shown for brevity) at a second frequency (e.g., about 100 kilo-Hertz to about 1 MegaHertz or higher, and preferably about 250 kilo Hertz) to a pair of electrodes and then measure or detect a second oscillating output signal from the third and fourth electrodes, which may involve measuring a second time differential $\Delta t_2$ (not shown) between the first input and output oscillating signals. From these signals, the system estimates a physical characteristic (e.g., hematocrit) of the fluid sample based on the first and second time differentials $\Delta t_1$ and $\Delta t_2$. Thereafter, the system is able to derive a glucose concentration. The estimate of the physical characteristic (e.g., hematocrit) can be done by applying an equation of the form $$HCT_{EST} = \frac{(C_1 \Delta t_1 - C_2 \Delta t_2 - C_3)}{m_1} \quad\quad \text{Eq. 4.1}$$

where each of $C_1$, $C_2$, and $C_3$ is an operational constant for the test strip and $m_1$ represent a parameter from regressions data.

Details of this exemplary technique can be found in Provisional U.S. Patent Application Ser. No. 61/530,795 filed on Sep. 2, 2011, entitled, "Hematocrit Corrected Glucose Measurements for Electrochemical Test Strip Using Time Differential of the Signals", which is hereby incorporated by reference.

Another technique to determine physical characteristic (e.g., hematocrit) can be by two independent measurements of physical characteristic (e.g., hematocrit). This can be obtained by determining: (a) the impedance of the fluid sample at a first frequency and (b) the phase angle of the fluid sample at a second frequency substantially higher than the first frequency. In this technique, the fluid sample is modeled as a circuit having unknown reactance and unknown resistance. With this model, an impedance (as signified by notation "|Z|") for measurement (a) can be determined from the applied voltage, the voltage across a known resistor (e.g., the intrinsic strip resistance), and the voltage across the unknown impedance Vz; and similarly, for measurement (b) the phase angle can be measured from a time difference between the input and output signals by those skilled in the art. Details of this technique is shown and described in provisional patent application Ser. No. 61/530,808 filed Sep. 2, 2011, which is incorporated by reference. Other suitable techniques for determining the physical characteristic (e.g., hematocrit, viscosity, temperature or density) of the fluid sample can also be utilized such as, for example, U.S. Pat. No. 4,919,770, U.S. Pat. No. 7,972,861, US Patent Application Publication Nos. 2010/0206749, 2009/0223834, or "Electric Cell—Substrate Impedance Sensing (ECIS) as a Noninvasive Means to Monitor the Kinetics of Cell Spreading to Artificial Surfaces" by Joachim Wegener, Charles R. Keese, and Ivar Giaever and published by Experimental Cell Research 259, 158-166 (2000) doi:10.1006/excr.2000.4919, available online at http://www.idealibray.coml; "Utilization of AC Impedance Measurements for Electrochemical Glucose Sensing Using Glucose Oxidase to Improve Detection Selectivity" by Takuya Kohma, Hidefumi Hasegawa, Daisuke Oyamatsu, and Susumu Kuwabata and published by Bull. Chem. Soc. Jpn. Vol. 80, No. 1, 158-165 (2007), all of these documents are incorporated by reference.

Another technique to determine the physical characteristic (e.g., hematorcrits, density, or temperature) can be obtained by knowing the phase difference (e.g., phase angle) and magnitude of the impedance of the sample. In one example, the following relationship is provided for the estimate of the physical characteristic or impedance characteristic of the sample ("IC"):

$$IC = M^2 * y_1 + M * y_2 + y_3 + P^2 * y_4 + P * y_5 \qquad \text{Eq. 4.2}$$

where:
M represents a magnitude |Z| of a measured impedance in ohms);
P represents a phase difference between the input and output signals (in degrees)
$y_1$ is about −3.2e−08 and ±10%, 5% or 1% of the numerical value provided hereof (and depending on the frequency of the input signal, can be zero);
$y_2$ is about 4.1e-03 and ±10%, 5% or 1% of the numerical value provided hereof (and depending on the frequency of the input signal, can be zero);
$y_3$ is about −2.5e+01 and ±10%, 5% or 1% of the numerical value provided hereof;
$y_4$ is about 1.5e-01 and ±10%, 5% or 1% of the numerical value provided hereof (and depending on the frequency of the input signal, can be zero); and
$y_5$ is about 5.0 and ±10%, 5% or 1% of the numerical value provided hereof (and depending on the frequency of the input signal, can be zero).

It is noted here that where the frequency of the input AC signal is high (e.g., greater than 75 kHz) then the parametric terms $y_1$ and $y_2$ relating to the magnitude of impedance M may be ±200% of the exemplary values given herein such that each of the parametric terms may include zero or even a negative value. On the other hand, where the frequency of the AC signal is low (e.g., less than 75 kHz), the parametric terms $y_4$ and $y_5$ relating to the phase angle P may be ±200% of the exemplary values given herein such that each of the parametric terms may include zero or even a negative value. It is noted here that a magnitude of H or HCT, as used herein, is generally equal to the magnitude of IC. In one exemplary implementation, H or HCT is equal to IC as H or HCT is used herein this application.

In another alternative implementation, Equation 4.3 is provided. Equation 4.3 is the exact derivation of the quadratic relationship, without using phase angles as in Equation 4.2.

$$IC = \frac{-y_2 + \left| \sqrt{y_2^2 - (4y_3(y_1 - M))} \right|}{2y_1} \qquad \text{Eq. 4.3}$$

where:
IC is the Impedance Characteristic [%];
M is the magnitude of impedance [Ohm];
$y_1$ is about 1.2292e1 and ±10%, 5% or 1% of the numerical value provided hereof
$y_2$ is about −4.3431e2 and ±10%, 5% or 1% of the numerical value provided hereof
$y_3$ is about 3.5260e4 and ±10%, 5% or 1% of the numerical value provided hereof.

By virtue of the various components, systems and insights provided herein, a technique to achieve an analyte measurement with output transient error trapping can be understood with reference to FIG. 6. This technique involves depositing a fluid sample (which may be a physiological sample or a control solution sample) on a biosensor at step 604 (e.g., in the form of a test strip as show in FIGS. 3A(1), 3A(2), 3A(3) through 3F) that has been inserted into a meter (step 602). Once the meter 200 is turned on, a signal is applied to the strip 100 (or its variants) and when the sample is deposited onto the test chamber, the applied signal (in conjunction with the appropriate reagent) physically transforms the analyte (e.g., glucose) in the sample into a different physical form (e.g., gluconic acid) due to the enzymatic reaction of the analyte with the reagent in the test chamber. As the sample flows into the capillary channel of the test cell, at least one physical characteristic of the sample is obtained from an output of another signal driven into the sample (step 608) along with estimate of the analyte concentration (step 610). From the obtained physical characteristic (step 608) and estimated analyte concentration (step 610), a specified sampling time Tsst is defined (at step 612) at which the signal output (due to electrons transfer shown in Equations 1 and 2) from the sample during the test sequence is measured (at step 614) and used for calculating the analyte concentration in step 616. In particular, the step of obtaining the physical characteristic (step 608) may include applying a first signal to the sample to measure a physical characteristic of the sample, while the step 606 of initiating an enzymatic reaction may involve driving a second signal to the sample, and the step of measuring (step 614) may entail evaluating an output signal from the third and fourth electrodes at a point in time after the start of the test sequence, in which the point in time is set (at step 612) as a function of at least the measured or estimated physical characteristic (step 608) and estimated analyte concentration (step 610).

The determination of the appropriate point (or time interval) Tsst during the test sequence $T_S$ as a function of the measured or estimated physical characteristic(s) (in step 612) can be determined by the use of a look-up table programmed into the microprocessor of the system. For example, a look-up table may be provided that allows for the system to select the appropriate sampling time Tsst for the analyte (e.g., glucose or ketone) with measured or known physical characteristic (e.g., hematocrit or viscosity) of the sample.

In particular, an appropriate sampling time point may be based on an early estimation of the analyte and the measured or known physical characteristic to arrive at the appropriate sampling time that gives the lowest error or bias as compared to referential values. In this technique, a look up table is provided in which the defined sampling time point is correlated to (a) the estimated analyte concentration and (b) the physical characteristic of the sample. For example, Table 1 may be programmed into the meter to provide a matrix in which qualitative categories (low, medium, and high glucose) of the estimated analyte form the main column and the qualitative categories (low, medium, and high) of the measured or estimated physical characteristic form the header row. In the second column, t/Hct is a value determined experimentally of the time shift per % hematocrit difference from nominal hematocrit of 42%. As one example, for 55% hematocrit at "Mid-Glucose" would indicate a time shift of (42−55)*90=−1170 ms. The time of −1170 milliseconds is added to the original test time of about 5000 milliseconds giving (5000−1170=3830 milliseconds)~3.9 seconds.

TABLE 1

| Estimated Analyte | t/Hct (in milliseconds) | Specified sampling time Tsst for Lo Hct (from start of test sequence, in seconds) | Specified sampling time Tsst for Mid Hct (from start of test sequence, in seconds) | Specified sampling time Tsst for High Hct (from start of test sequence, in seconds) |
|---|---|---|---|---|
| Lo-Glucose | 40 | 5.5 | 5 | 4.5 |
| Mid-Glucose | 90 | 6.1 | 5 | 3.9 |
| Hi-Glucose | 110 | 6.3 | 5 | 3.6 |

The time Tsst (i.e., a specified sampling time) at which the system should be sampling or measuring the output signal of the biosensor is based on both the qualitative category of the estimated analyte and measured or estimated physical characteristic and is predetermined based on regression analysis of a large sample size of actual physiological fluid samples. Applicants note that the appropriate sampling time is measured from the start of the test sequence but any appropriate datum may be utilized in order to determine when to sample the output signal. As a practical matter, the system can be programmed to sample the output signal at an appropriate time sampling interval during the entire test sequence such as for example, one sampling every 100 milliseconds or even as little as about 1 milliseconds. By sampling the entire signal output transient during the test sequence, the system can perform all of the needed calculations near the end of the test sequence rather than attempting to synchronize the sampling time with the set time point, which may introduce timing errors due to system delay.

Applicant hereafter will discuss the look-up Table 1 in relation to the particular analyte of glucose in physiological fluid samples. Qualitative categories of blood glucose are defined in the first column of Table 1 in which low blood glucose concentrations of less than about 70 mg/dL are designated as "Lo-Glucose"; blood glucose concentrations of higher than about 70 mg/dL but less than about 250 mg/dL are designated as "Mid-Glucose"; and blood glucose concentrations of higher than about 250 mg/dL are designated as "Hi-Glucose".

During a test sequence, an "Estimated Analyte" can be obtained by sampling the signal at a convenient time point, typically at five seconds during a typical 10 seconds test sequence. The measurement sampled at this five second time point allows for an accurate estimate of the analyte (in this case blood glucose). The system may then refer to a look-up table (e.g., Table 1) to determine when to measure the signal output from the test chamber at a specified sampling time Tsst based on two criteria: (a) estimated analyte and (b) qualitative value of the physical characteristic of the sample. For criteria (b), the qualitative value of the physical characteristic is broken down into three sub-categories of Low Hct, Mid Hct and High Hct. Thus, in the event that the measured or estimated physical characteristic (e.g., hematocrit) is high (e.g., greater than 46%) and the estimated glucose is also high, then according to Table 1, the test time for the system to measure the signal output of test chamber would be about 3.6 seconds. On the other hand, if the measured hematocrit is low (e.g., less than 38%) and the estimated glucose is low then according to Table 1, the specified sampling time Tsst for the system to measure the signal output of test chamber would be about 5.5 seconds.

Once the signal output $I_T$ of the test chamber is measured at the specified sampling time Tss (which is governed by the measured or estimated physical characteristic), the signal $I_T$ is thereafter used in the calculation of the analyte concentration (in this case glucose) with Equation 5 below.

$$G_0 = \left[ \frac{I_T - \text{Intercept}}{\text{Slope}} \right] \qquad \text{Eq. 5}$$

where $G_0$ represents an analyte concentration;

$I_T$ represents a signal (proportional to analyte concentration) determined from the sum of the end signals measured at a specified sampling time Tsst, which may be the total current measured at the specified sampling time Tsst;

Slope represents the value obtained from calibration testing of a batch of test strips of which this particular strip comes from and is typically about 0.02; and Intercept represents the value obtained from calibration testing of a batch of test strips of which this particular strip comes from and is typically from about 0.6 to about 0.7.

It should be noted that the step of applying the first signal and the driving of the second signal is sequential in that the order may be the first signal then the second signal or both signals overlapping in sequence; alternatively, the second signal first then the first signal or both signals overlapping in sequence. Alternatively, the applying of the first signal and the driving of the second signal may take place simultaneously.

In the method, the step of applying of the first signal involves directing an alternating signal provided by an appropriate power source (e.g., the meter 200) to the sample so that a physical characteristic of the sample is determined from an output of the alternating signal from the sample. The physical characteristic being detected may be one or more of viscosity, hematocrit or density. The directing step may include driving first and second alternating signal at different respective frequencies in which a first frequency is lower than the second frequency. Preferably, the first frequency is at least one order of magnitude lower than the second frequency. As an example, the first frequency may be any frequency in the range of about 10 kHz to about 100 kHz and the second frequency may be from about 250 kHz to about 1 MHz or more. As used herein, the phrase "alternating signal" or "oscillating signal" can have some portions of the signal alternating in polarity or all alternating current signal or an alternating current with a direct current offset or even a multi-directional signal combined with a direct-current signal.

Further refinements of Table 1 based on additional investigations of the technique allowed applicants to devise Table 2, shown below.

TABLE 2

Specified sampling time Tsst to Estimated G and Measured or Estimated Physical Characteristic

| Estimated G | Measured or Estimated Physical Characteristic (e.g., HCT [%]) | | | | | | | | | | | | |
|---|---|---|---|---|---|---|---|---|---|---|---|---|---|
| [mg/dL] | 24 | 27 | 30 | 33 | 36 | 39 | 42 | 45 | 48 | 51 | 54 | 57 | 60 |
| 25 | 4.6 | 4.6 | 4.5 | 4.4 | 4.4 | 4.4 | 4.3 | 4.3 | 4.3 | 4.2 | 4.1 | 4.1 | 4.1 |
| 50 | 5 | 4.9 | 4.8 | 4.7 | 4.7 | 4.6 | 4.5 | 4.4 | 4.3 | 4.2 | 4.1 | 4 | 4 |
| 75 | 5.3 | 5.3 | 5.2 | 5 | 4.9 | 4.8 | 4.7 | 4.5 | 4.4 | 4.3 | 4.1 | 4 | 3.8 |
| 100 | 5.8 | 5.6 | 5.4 | 5.3 | 5.1 | 5 | 4.8 | 4.6 | 4.4 | 4.3 | 4.1 | 3.9 | 3.7 |
| 125 | 6.1 | 5.9 | 5.7 | 5.5 | 5.3 | 5.1 | 4.9 | 4.7 | 4.5 | 4.3 | 4.1 | 3.8 | 3.6 |
| 150 | 6.4 | 6.2 | 5.9 | 5.7 | 5.5 | 5.3 | 5 | 4.8 | 4.6 | 4.3 | 4 | 3.8 | 3.5 |
| 175 | 6.6 | 6.4 | 6.2 | 5.9 | 5.6 | 5.4 | 5.2 | 4.9 | 4.6 | 4.3 | 4 | 3.7 | 3.4 |
| 200 | 6.8 | 6.6 | 6.4 | 6.1 | 5.8 | 5.5 | 5.2 | 4.9 | 4.6 | 4.3 | 4 | 3.7 | 3.4 |
| 225 | 7.1 | 6.8 | 6.5 | 6.2 | 5.9 | 5.6 | 5.3 | 5 | 4.7 | 4.3 | 4 | 3.6 | 3.2 |
| 250 | 7.3 | 7 | 6.7 | 6.4 | 6 | 5.7 | 5.3 | 5 | 4.7 | 4.3 | 4 | 3.6 | 3.2 |
| 275 | 7.4 | 7.1 | 6.8 | 6.4 | 6.1 | 5.8 | 5.4 | 5 | 4.7 | 4.3 | 4 | 3.5 | 3.2 |
| 300 | 7.5 | 7.1 | 6.8 | 6.5 | 6.2 | 5.8 | 5.5 | 5.1 | 4.7 | 4.3 | 4 | 3.5 | 3.1 |
| w325 | 7.6 | 7.3 | 6.9 | 6.5 | 6.2 | 5.8 | 5.5 | 5.1 | 4.7 | 4.3 | 3.9 | 3.5 | 3.1 |
| 350 | 7.6 | 7.3 | 7 | 6.6 | 6.2 | 5.8 | 5.5 | 5.1 | 4.7 | 4.3 | 3.9 | 3.5 | 3.1 |
| 375 | 7.7 | 7.3 | 7 | 6.6 | 6.2 | 5.8 | 5.5 | 5.1 | 4.7 | 4.3 | 3.9 | 3.5 | 3.1 |
| 400 | 7.7 | 7.3 | 6.9 | 6.5 | 6.2 | 5.8 | 5.4 | 5 | 4.7 | 4.3 | 3.9 | 3.5 | 3.1 |
| 425 | 7.6 | 7.3 | 6.9 | 6.5 | 6.2 | 5.8 | 5.4 | 5 | 4.6 | 4.3 | 3.8 | 3.5 | 3.1 |
| 450 | 7.6 | 7.2 | 6.8 | 6.4 | 6.1 | 5.7 | 5.3 | 5 | 4.6 | 4.3 | 3.8 | 3.5 | 3.1 |
| 475 | 7.4 | 7.1 | 6.7 | 6.4 | 6 | 5.6 | 5.3 | 4.9 | 4.6 | 4.2 | 3.8 | 3.5 | 3.1 |
| 500 | 7.3 | 7 | 6.6 | 6.2 | 5.9 | 5.5 | 5.2 | 4.9 | 4.5 | 4.1 | 3.8 | 3.5 | 3.2 |
| 525 | 7.1 | 6.8 | 6.5 | 6.1 | 5.8 | 5.5 | 5.1 | 4.8 | 4.4 | 4.1 | 3.8 | 3.5 | 3.2 |
| 550 | 7 | 6.7 | 6.3 | 5.9 | 5.6 | 5.3 | 5 | 4.7 | 4.4 | 4.1 | 3.8 | 3.5 | 3.2 |
| 575 | 6.8 | 6.4 | 6.1 | 5.8 | 5.5 | 5.2 | 4.9 | 4.6 | 4.3 | 4.1 | 3.8 | 3.5 | 3.4 |
| 600 | 6.5 | 6.2 | 5.9 | 5.6 | 5.3 | 5 | 4.7 | 4.5 | 4.3 | 4 | 3.8 | 3.6 | 3.4 |

As in Table 1, a measured or estimated physical characteristic is used in Table 2 along with an estimated analyte concentration to derive a time Tsst at which the sample is to be measured. For example, if the measured characteristic is about 30% and the estimated glucose (e.g., by sampling at about 2.5 to 3 seconds) is about 350, the time at which the microcontroller should sample the fluid is about 7 seconds. In another example, where the estimated glucose is about 300 mg/dL and the measured or estimated physical characteristic is 60%, the specified sampling time would be about 3.1 seconds.

For the embodiments utilized with Table 2, the estimated glucose concentration is provided with an equation:

$$G_{est} = \frac{(I_E - x_2)}{x_1} \quad \text{Eq. 6}$$

where $G_{est}$ represents the estimated glucose concentration;

$I_E$ is the signal measured at the predetermined sampling time;

$x_1$ is the slope (e.g., $x_1 = 1.3e01$);

$x_2$ is the intercept (e.g., $x_2 = 6.9e02$)

From the estimated glucose, the glucose concentration can be determined from:

$$G_0 = \frac{(I_s - x_4)}{x_3} \quad \text{Eq. 7}$$

where:

$G_O$ represents the glucose concentration;

$I_S$ is the signal measured at a specified sampling time Tsst from Table 2;

$x_3$ is the slope (e.g., $x_3 = 9.6$); and $x_4$ is the intercept (e.g., $x_4 = 4.8e02$).

Although applicant's technique may specify only one sampling time point, the method may include sampling as many time points as required, such as, for example, sampling the signal output continuously (e.g., at specified sampling time Tsst such as, every 1 milliseconds to 100 milliseconds) from the start of the test sequence until at least about 10 seconds after the start and the results stored for processing near the end of the test sequence. In this variation, the sampled signal output at the specified sampling time Tsst (which may be different from the predetermined sampling time point) is the value used to calculate the analyte concentration.

Figure 7:
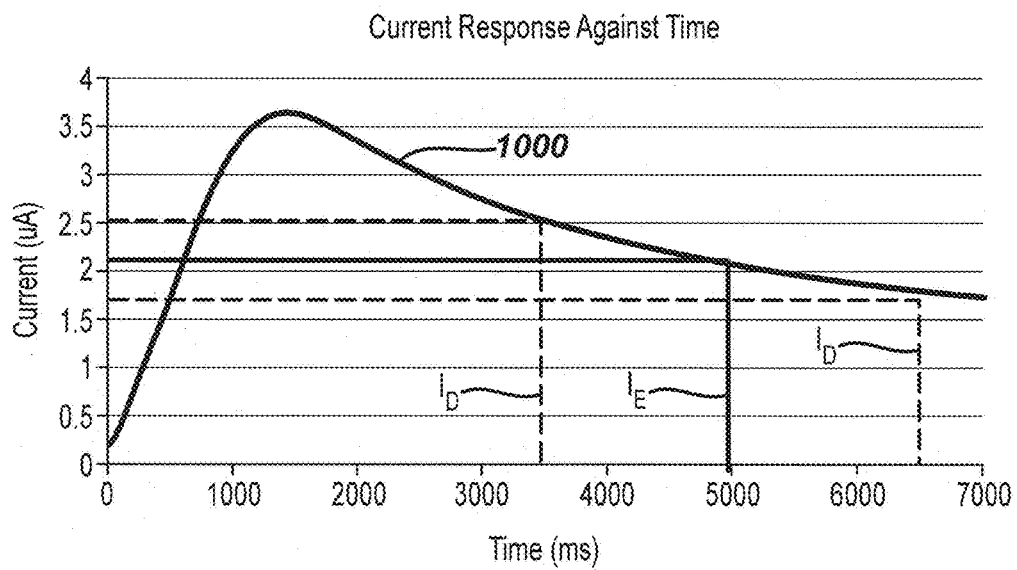
FIG. 7 illustrates a signal output transient of the biosensor and the range of time point utilized for determination of the analyte, as well as the estimation of the analyte concentration.
Figure 8:
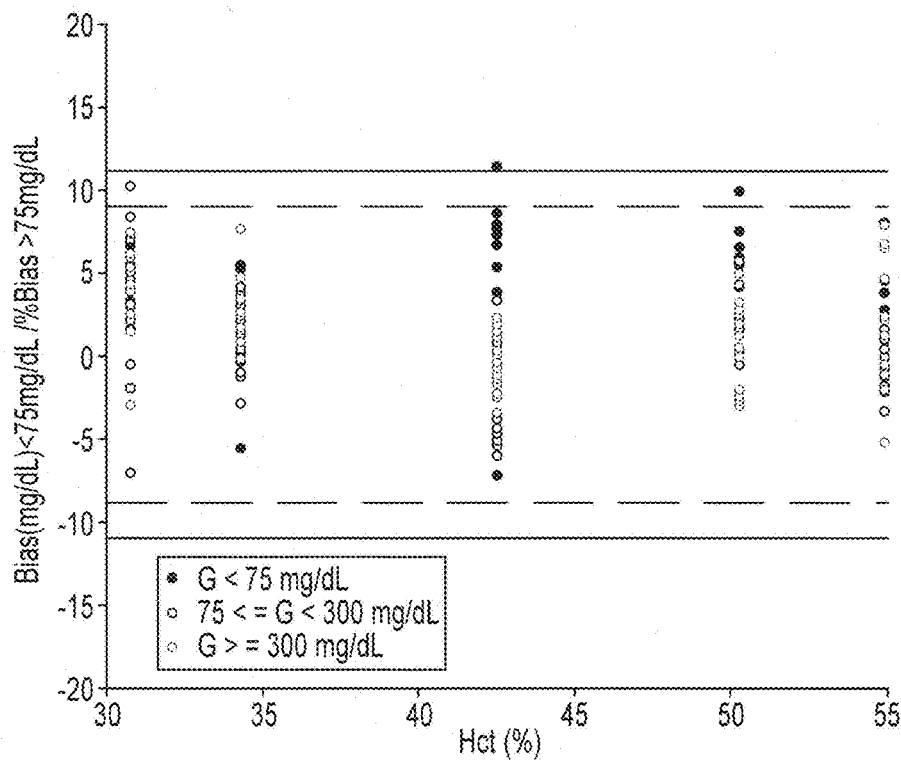
FIG. 8 illustrates data from test measurements conducted with the exemplary technique herein such that the data show the bias of less than about ±10% for the hematocrit range of about 30% to about 55%.

It is noted that in the preferred embodiments, the measurement of a signal output for the value that is somewhat proportional to analyte (e.g., glucose) concentration is performed prior to the estimation of the hematocrit. Alternatively, the hematocrit level can be estimated prior to the measurement of the preliminary glucose concentration. In either case, the estimated glucose measurement $G_E$ is obtained by Equation 3.3 with $I_E$ sampled at about one of 2.5 seconds or 5 seconds, as in FIG. 7, the physical characteristic (e.g., Hct) is obtained by Equation 4 and the glucose measurement G is obtained by using the measured signal output $I_D$ at the designated sampling time point(s) (e.g., the measured signal output $I_D$ being sampled at 3.5 seconds or 6.5 seconds) for the signal transient 1000.

Other techniques for determining the analyte concentration or value are shown and described in PCT/GB2012/053276 filed on Dec. 28, 2012, PCT/GB2012/053279 filed on Dec. 28, 2012; PCT/GB2012/053277 filed on Dec. 28, 2012, all of the applications are hereby incorporated by reference as if fully set forth herein with a copy attached to the appendix of this application.

In the biosensors described herein, I have identified anomalous output signal transients that are believed to be caused by a problematic counterelectrode or reference electrode. In particular, it has been determined that if the carbon surface of the counter electrode is defective in terms of its surface profile, area, coverage, or geometry (i.e., "fouling"), the biosensor would generate these anomalous output signal transients for each of the working electrodes (WE1 for first working electrode and WE2 for second working electrode), shown for example in FIG. 4C. In FIG. 4C, it can be that the normal transient for each working electrode follows a first order curve with a clear peak in magnitude from around 1200 nanoamps to 1600 nanoamps whereas the anomalous transients are generally of a flatter curve of much lower magnitudes from about 400 nanoamps to about 700 nanoamps.

As shown in Table 3, three anomalous measurements were identified: L53, L60 and L113 measurements. In these anomalous measurements, it can be seen that these measurements have a common characteristic in that whenever a differential ΔI is taken of each output signal at the specified sampling time and a predetermined sampling time, the differential ΔI in the magnitude for a true positive of a defective biosensor, tend to be less than 100 nanoamperes. For the second working electrode measurements of L53, L60 and L113, all of the magnitude differentials were less than 100 nanoamperes for the second working electrode. For first electrode measurements of L53 and L113, the magnitude differentials ΔI were under 100 nanoamperes. Although the magnitude of the differential ΔI for the first working electrode measurement (i.e., measurement L60) was greater than 100 nanoamperes (at 151 nanoamperes), it was nevertheless decided that only one working electrode is (i.e., the second working electrode at 61 nA) would be needed to trigger this error flag or trap. I have conducted tests to determine the optimum threshold to trigger this error flag or trap. Where the threshold was defined to be greater than 100 nanoamperes, the number of false positives began to match the number of true positives and at a certain threshold, i.e., 150 nanoamps, the false positive exceeded the true positives at almost 12 times (i.e., 36 true positives compared to 431 false positives). Although 100 nanoamps is indicated as the preferred threshold for the biosensor configurations described here, other thresholds can be utilized as long as the number of false positives is 70% or less of the true positives.

TABLE 3

| Anomalous Transient Identification | Iwe1@Tpst (in ηA) | IWe1@Tsst (in ηA) | ΔI for we1 (in ηA) | Iwe2@Tpst (in ηA) | Iwe2@Tsst (in ηA) | ΔI for we2 (in ηA) |
|---|---|---|---|---|---|---|
| L53 | 631 | 537 | 94 | 537 | 504 | 33 |
| L60 | 755 | 604 | 151 | 629 | 568 | 61 |
| L113 | 882 | 800 | 82 | 776 | 809 | −33 |

To ensure that these anomalous output signals are identified in order to provide error signaling to the user, I have devised a technique that compares the difference between the current on each working electrode at a predetermined sampling time (e.g., 2.5 seconds from the start) and at a specified sampling time described earlier. If this difference (in magnitudes at two sampling times for each electrode) is less than a predetermined threshold or value, the error flagging or trapping is activated. As noted earlier, the predetermined threshold was selected based on experiments that would guarantee the trapping of several previously identified transients with low currents on both working electrodes, but limit the number of additional false positives generated at nominal test conditions.

Referring back to step 616 in FIG. 6, the system evaluates the signal output from each of the first and second working electrodes to determine if there is a problem with the counter or reference electrode 10. The mathematical representation of the evaluation that would trigger an error is shown by Eqs. 8.1 and 8.2:

$$M_1 = I_{we1@Tpst} - I_{we1@Tsst} \qquad \text{Eq. 8.1}$$

$$M_2 = I_{we2@Tpst} - I_{we2@Tsst} \qquad \text{Eq. 8.2}$$

where $M_1$ comprises a difference in magnitude of the output signals for the first working electrode;

$M_2$ comprises a difference in magnitude of the output signals for the second working electrode;

$I_{we1@Tpst}$ is the output signal of the first working electrode proximate a predetermined sampling time Tpst;

$I_{we1@Tsst}$ is the output signal of the first working electrode proximate the specified sampling time Tsst;

$I_{we2@Tpst}$ is the output signal of the second working electrode proximate a predetermined sampling time Tpst; and $I_{we2@Tsst}$ is the output signal of the second working electrode proximate the specified sampling time Tsst;

Error if m1<$Pred_{TH}$ or m2<$Pred_{TH}$;

Tsst is determined based on impedance measurement or estimated glucose measurement and Tpst is a predetermined sampling time (e.g., any time point or interval from about 2 seconds to about 7 seconds).

Applicant notes that the technique is designed so that if such output transient error is detected at step 616, the system will quickly annunciate an error (from step 616 directly to step 620) and return to the main routine (step 626) or terminate the assay process.

An alternative technique has also been devised by applicant that allows for the system to set an error flag (~1 state at step 617) while allowing the continuation of the acquisition of an analyte concentration and then terminating the assay only thereafter. In particular, this technique can be achieved with reference to step 616 which is used to evaluate the output transient signals from the working electrodes. If step 616 returns a true then the process moves to step 617 (instead of step 620) for the system to set an error flag. After the error flag has been set at 617, the system continues ahead to step 618 to calculate the analyte concentration using the measured output signals at Tsst. At step 623, the system checks to see if one or more error flags (besides the transient output error flag from step 617) have been set. If true, the system moves to step 620 to annunciate the error otherwise the analyte concentration is annunciated at step 624. Although this alternative technique does not provide an immediate feedback as in the other technique, it allows for the system to assess the number of error flag(s) being set before actually declaring that an error has occurred.

Figure 6A:
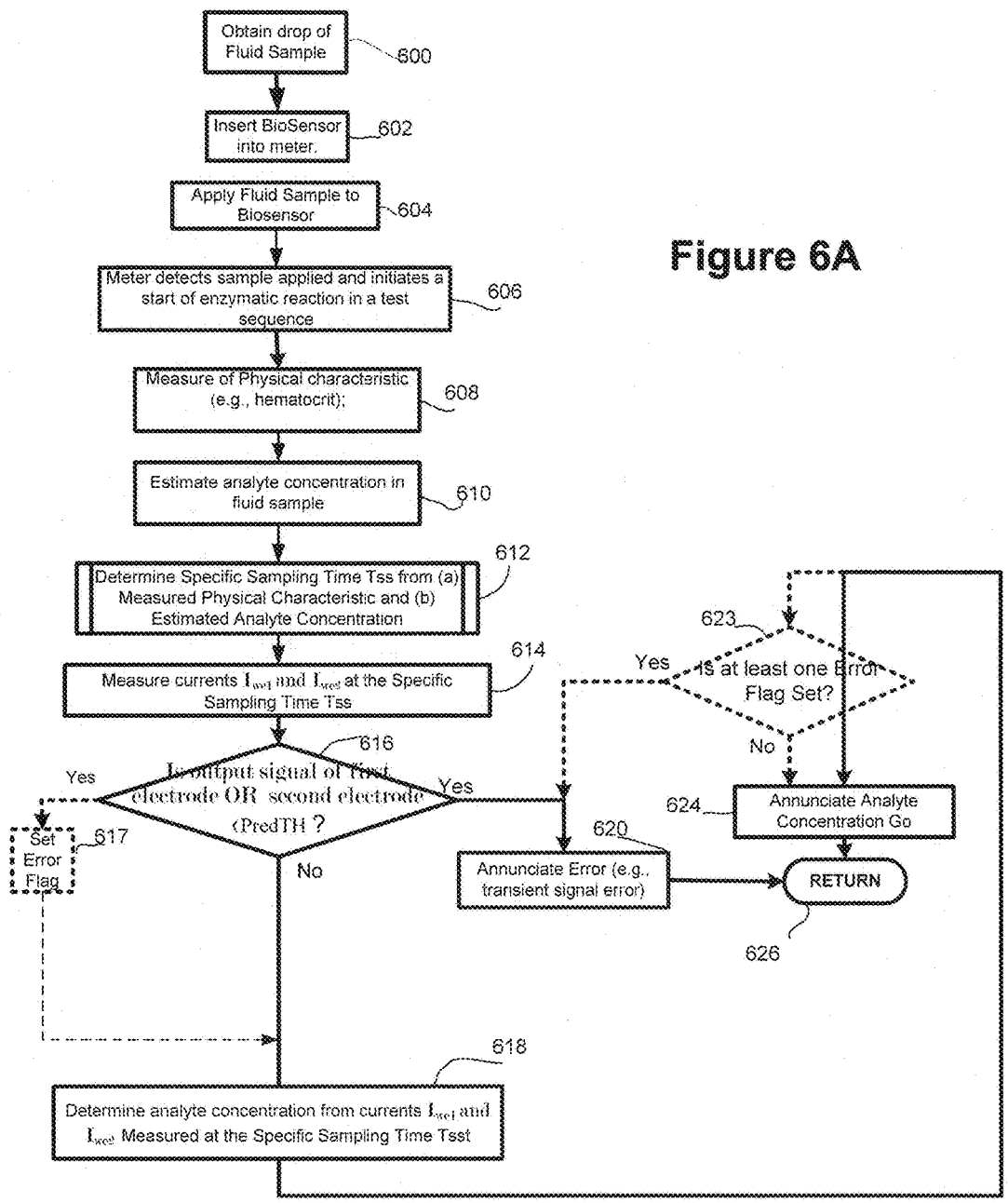
FIG. 6A illustrates a logic diagram of an exemplary method to achieve a more accurate analyte determination with error detection for insufficient sample fill of the biosensor.
Figure 6B:
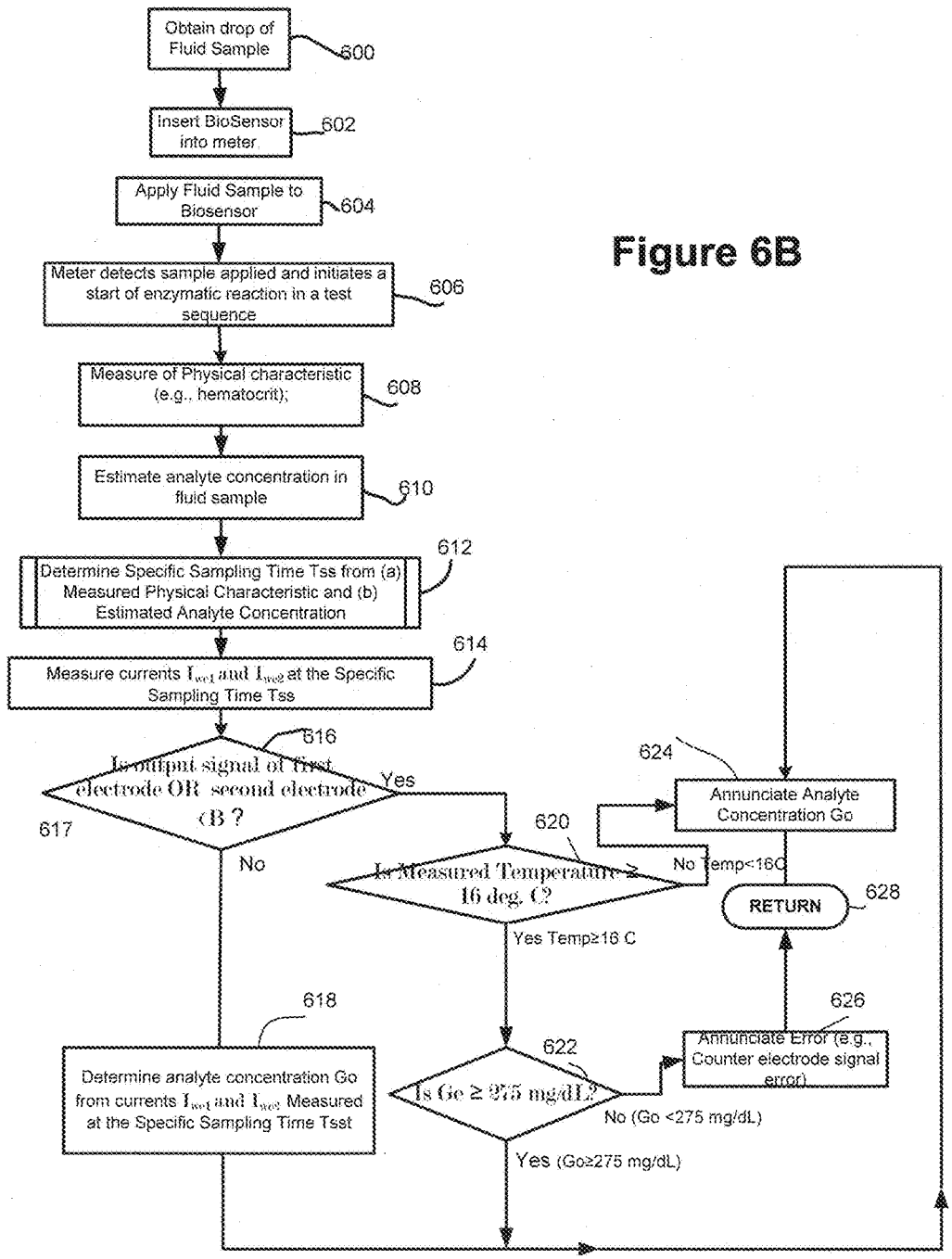
FIG. 6B illustrates an alternative logic to that of FIG. 6A.

The technique described in FIG. 6A can also be provided with other thresholds. For example, I have determined that at the temperature measured proximate the biosensor below 16 degrees Celsius, the expected error message should be bypassed or avoided to ensure that a large number of accurate glucose measurements below 16 degrees Celsius are not eliminated by my error trap technique. This can be seen in step 620 to step 624 of FIG. 6B when the measured temperature is below 16 degrees the logic moves directly to the annunciation of the glucose value (determined previously at step 618). Also, where the measured or estimated glucose Ge is at or greater than 275 mg/dL, the expected error message should also be bypassed to give the glucose results in steps 622 to step 624 otherwise if the estimated glucose Ge is less than 275 mg/dL then the expected error message would be given to the user.

Although the techniques described herein have been directed to determination of glucose, the techniques can also applied to other analytes (with appropriate modifications by those skilled in the art) that are affected by physical characteristic(s) of the fluid sample in which the analyte(s) is disposed in the fluid sample. For example, the physical characteristic (e.g., hematocrit, viscosity or density and the like) of a physiological fluid sample could be accounted for in determination of ketone or cholesterol in the fluid sample, which may be physiological fluid, calibration, or control fluid. Other biosensor configurations can also be utilized. For example, the biosensors shown and described in the following US Patents can be utilized with the various embodiments described herein: U.S. Pat. Nos. 6,179,979; 6,193,873; 6,284,125; 6,413,410; 6,475,372; 6,716,577; 6,749,887; 6,863,801; 6,860,421; 7,045,046; 7,291,256; 7,498,132, all of which are incorporated by reference in their entireties herein.

As is known, the detection of the physical characteristic does not have to be done by alternating signals but can be done with other techniques. For example, a suitable sensor can be utilized (e.g., US Patent Application Publication No. 20100005865 or EP1804048 B1) to determine the viscosity or other physical characteristics. Alternatively, the viscosity can be determined and used to derive for hematocrits based on the known relationship between hematocrits and viscosity as described in "Blood Rheology and Hemodynamics" by Oguz K. Baskurt, M.D., Ph.D., 1 and Herbert J. Meiselman, Sc.D., *Seminars in Thrombosis and Hemostasis*, volume 29, number 5, 2003.

As described earlier, the microcontroller or an equivalent microprocessor (and associated components that allow the microcontroller to function for its intended purpose in the intended environment such as, for example, the processor 300 in FIG. 2B) can be utilized with computer codes or software instructions to carry out the methods and techniques described herein. Applicants note that the exemplary microcontroller 300 (along with suitable components for functional operation of the processor 300) in FIG. 2B is embedded with firmware or loaded with computer software representative of the logic diagrams in FIG. 6 and the microcontroller 300, along with associated connector 220 and interface 306 and equivalents thereof, are the means for: (a) determining a specified sampling time based on a sensed or estimated physical characteristic, the specified sampling time being at least one time point or interval referenced from a start of a test sequence upon deposition of a sample on the test strip and (b) determining an analyte concentration based on the specified sampling time. Alternatively, the means for determining may include means for applying a first signal to the plurality of electrodes so that a batch slope defined by a physical characteristic of a fluid sample is derived and for applying a second signal to the plurality of electrodes so that an analyte concentration is determined based on the derived batch slope and the specified sampling time. Furthermore, the means for determining may include means for estimating an analyte concentration based on a predetermined sampling time point from the start of the test sequence and for selecting a specified sampling time from a matrix of estimated analyte concentration and sensed or estimated physical characteristic. Yet further, the means for determining may include means for selecting a batch slope based on the sensed or estimated physical characteristic and for ascertaining the specified sampling time from the batch slope.

Moreover, while the invention has been described in terms of particular variations and illustrative Figures, those of ordinary skill in the art will recognize that the invention is not limited to the variations or Figures described. In addition, where methods and steps described above indicate certain events occurring in certain order, it is intended that certain steps do not have to be performed in the order described but in any order as long as the steps allow the embodiments to function for their intended purposes. Therefore, to the extent there are variations of the invention, which are within the spirit of the disclosure or equivalent to the inventions found in the claims, it is the intent that this patent will cover those variations as well.

The invention claimed is:

1. A glucose measurement system comprising:
a test strip including:
a substrate;
a plurality of electrodes connected to respective electrode connectors; and a glucose meter including:
a housing;
a test strip port connector configured to connect to the respective electrode connectors of the test strip; and
a microprocessor in electrical communication with the test strip port connector to apply electrical signals or sense electrical signals from the plurality of electrodes, wherein the microprocessor is configured to:
(a) apply a first signal to a first electrode and a second electrode of the plurality of electrodes so that a hematocrit level of a sample is determined;
(b) estimate a glucose concentration based on a signal output measured at a predetermined sampling time during a test sequence for each of the first and second electrodes;
(c) apply a second signal to the first electrode and the second electrode of the plurality of electrodes at a specified sampling time during the test sequence, wherein the specified sampling time is determined by looking up the determined hematocrit level and the estimated glucose concentration of the fluid sample in a stored look-up table, the look-up table comprising different hematocrit levels and different estimated glucose concentrations indexed against different specified sampling times
(d) measure a signal output at the specified sampling time for each the first and second electrodes;
(e) evaluate, for each of the first and second electrodes, whether a difference between respective magnitudes of the signal output at the specified sampling time and the predetermined sampling time is less than a predetermined threshold;
(f) if the difference for each electrode is equal to or greater than the predetermined threshold then determine or calculate the glucose concentration from the signal outputs of the first and second electrodes at the specified sampling time and annunciate the glucose concentration; and
(g) if the difference in magnitude for each electrode is less than the predetermined threshold then annunciate an error.

2. A glucose measurement system comprising:
a test strip including:
a substrate;
a plurality of electrodes connected to respective electrode connectors; and
a glucose meter including:
a housing;
a test strip port connector configured to connect to the respective electrode connectors of the test strip; and
a microprocessor in electrical communication with the test strip port connector to apply electrical signals or sense electrical signals from the plurality of electrodes, wherein the microprocessor is configured to:
(a) apply a first signal to a first electrode and a second electrode of the plurality of electrodes so that a hematocrit level of a fluid sample is determined;

(b) estimate a glucose concentration based on a signal output measured at a predetermined sampling time during a test sequence for each first and second electrodes;

(c) apply a second signal to the first electrode and the second electrode of the plurality of electrodes at a specified sampling time during the test sequence, wherein the specified sampling time is determined by looking up the determined hematocrit level and the estimated glucose concentration of the fluid sample in a stored look-up table, the look-up table comprising different hematocrit levels and different estimated glucose concentrations indexed against different sampling times (d) measure a signal output at the specified sampling time for each first and second electrodes;

(e) evaluate, for each of the first and second electrodes, whether a difference in a magnitude of the signal output at the specified sampling time and the predetermined sampling time is less than a predetermined threshold;

(f) if the difference in magnitude for each electrode is less than predetermined threshold then set an error flag as active;

(g) determine or calculate the glucose concentration from the signal outputs of the first and second electrodes at the specified sampling time;

(h) if the error flag is set then terminate the process; and (i) if the difference in magnitude for each electrode is greater than the predetermined threshold then annunciate the glucose concentration.

3. A glucose analyte measurement system comprising: a test strip including:

a substrate;

a plurality of electrodes connected to respective electrode connectors; and a glucose meter including:

a housing;

a test strip port connector configured to connect to the respective electrode connectors of the test strip; and a microprocessor in electrical communication with the test strip port connector to apply electrical signals or sense electrical signals from the plurality electrodes, wherein the microprocessor is configured to:

(a) apply a first signal to a first electrode and a second electrode of the plurality of electrodes so that a hematocrit level of a fluid sample is determined;

(b) estimate a glucose concentration based on a signal output measured at a predetermined sampling time during a test sequence for each of first and second electrodes;

(c) apply a second signal to the first electrode and the second electrode of the plurality of electrodes at a specified sampling time during the test sequence, wherein the specified sampling time is determined by looking up the determined hematocrit level and the estimated glucose concentration of the fluid sample in a look-up table, the look-up table comprising different hematocrit levels and different estimated glucose concentrations indexed against different sampling times;

(d) measure a signal output at the specified sampling time for each of the first and second electrodes;

(e) evaluate whether a magnitude of a difference between output signals at the specified sampling time and the predetermined sampling time for each working electrode is greater than a predetermined threshold and if true calculate a glucose concentration for the sample, otherwise if false annunciate an error or set an error flag; and (f) determine whether the magnitude of the output signal for each working electrode at an offset time interval before the specified sampling time is less than the magnitude for the corresponding working electrode at the specified sampling time and if true annunciate an error or set an error flag active.

4. The system of claim 2, in which a mathematical evaluation for triggering the error flag comprises:

$$M_1 = I_{we1@Tpst} - I_{we1@Tsst}$$

$$M_2 = I_{we2@Tpst} - I_{we2@Tsst}$$

where $M_1$ comprises a difference in magnitude of the output signals for the first working electrode;

$M_2$ comprises a difference in magnitude of the output signals for the second working electrode;

$I_{we1@Tpst}$ is the output signal of the first working electrode proximate a predetermined sampling time Tpst;

$I_{we1@Tsst}$ is the output signal of the first working electrode proximate the specified sampling time Tsst;

$I_{we2@Tpst}$ is the output signal of the second working electrode proximate a predetermined sampling time Tpst; and $I_{we2@Tsst}$ is the output signal of the second working electrode proximate the specified sampling time Tsst.

5. The system of one of claims 1-3, in which the plurality of electrodes comprises first through fifth electrodes with the first and second electrode to measure the glucose concentration and third and fourth electrodes to measure the hematocrit level and the fifth electrode comprises a reference electrode.

6. The system of one of claims 1-3, in which the plurality of electrodes comprises first through fifth electrodes disposed in the same chamber provided on the substrate.

7. The system of claim 5, in which the first and second electrodes and third and fourth electrodes are disposed in respective two different chambers provided on the substrate.

8. The system of claim 5, in which all of the electrodes are disposed on the same plane defined by the substrate.

9. The system of claim 5, in which a reagent is disposed proximate the at least two other electrodes and no reagent is disposed on the third and fourth electrodes.

10. The system of claim 5, in which the glucose concentration is determined from the second signal within about 10 seconds of a start of the test sequence and the predetermined sampling time comprises the predetermined sampling time from the start of the test measurement sequence.

11. The system of one of claims 1-3, in which the microcontroller determines the glucose concentration with an equation of the form:

$$G_0 = \left[\frac{I_T - \text{Intercept}}{\text{Slope}}\right]$$

Where $G_0$ represents a glucose concentration;

$I_T$ represents the output signals measured at the SpecifiedSamplingTime;

Slope represents the calibration slope value obtained from calibration testing of a batch of test strips of which this particular strip comes from; and Intercept represents the calibration intercept value obtained from calibration testing of a batch of test strips of which this particular strip comes from.

12. The system of one of claims 1-3, in which the microcontroller estimates the glucose concentration with an equation of the form:

$$G_{est} = \frac{(I_E - x_2)}{x_1}$$

where $G_{est}$ represents the estimated glucose concentration;
$I_E$ is the signal measured at the predetermined sampling time
$X_1$ comprises a calibration slope of a particular batch of biosensors;
$X_2$ comprises a calibration intercept of a particular batch of biosensors; and
in which the microcontroller determines the glucose concentration with an equation of the form:

$$G_0 = \frac{(I_s - x_4)}{x_3}$$

where: $G_O$ represents the glucose concentration;
$I_S$ comprises the signal measured at the specified sampling time;
$X_3$ comprises a calibration slope of a particular batch of biosensors; and
$X_4$ comprises the intercept of a particular batch of biosensors.

13. The system of claim 5, in which the predetermined threshold comprises about 100 nanoamperes.

14. The system of claim 13, in which the microcontroller is configured to determine if a temperature measured proximate the microcontroller is greater than a predetermined temperature and if an estimate of the glucose concentration is at or greater than a predetermined glucose threshold.

15. The system of claim 14, in which the microcontroller annunciates the glucose concentration if the measured temperature is less than the predetermined temperature and any of the differences in magnitudes is less than the predetermined threshold.

16. The system of claim 14, in which the microcontroller annunciates an error if any of the differences in magnitudes is less than the predetermined threshold and the measured temperature is at or above the predetermined temperature and glucose concentration estimate is less than a predetermined value.

17. The system of claim 14, in which the microcontroller annunciates the glucose concentration if any of the differences in magnitudes is less than the predetermined threshold and the measured temperature is less than the predetermined value and annunciates the glucose concentration if any of the differences in magnitudes is less than the predetermined threshold and the measured temperate at or greater than the predetermined temperature and the estimated glucose concentration is at or greater than the predetermined value.

18. A method of determining current transient output error in a biosensor having a plurality of electrodes with first, second, third and fourth electrodes, the method comprising the steps of:
applying a first signal to the first and second electrodes;
depositing a fluid sample proximate the first, second, third and fourth electrodes;
applying a second signal to the third and fourth electrodes;
determining a hematocrit level of the fluid sample from an output signal of the third and fourth electrodes;
defining a specified sampling time based on the hematocrit level of the sample, wherein the specified sampling time is determined by looking up determined hematocrit level and an estimated glucose concentration of the sample in a look-up table, the look-up table comprising different hematocrit levels and different estimated glucose concentrations indexed against different sampling times
initiating an electrochemical reaction between the first and second electrodes and glucose in a fluid sample to start a test sequence for a transformation of the glucose into an enzymatic-byproduct;
measuring signal outputs at the specified sampling time from each of the first and second electrodes during the electrochemical reaction;
evaluating, for each of the first and second electrodes, whether a difference in respective magnitudes of the output signal at the specified sampling time and the output signal at the predetermined sampling time is less than a predetermined threshold;
if the evaluating is true then annunciate an output transient error and terminate test sequence;
if the evaluating step is false then calculating a glucose concentration representative of a quantity of the glucose in the fluid sample from the signal outputs; and
annunciating the glucose concentration.

19. The method of claim 18, in which the calculating step comprises:
estimating a glucose concentration based on a predetermined sampling time point from the start of the test sequence;
selecting a specified sampling time based on both the measured or estimated hematocrit level and the estimated glucose concentration.

* * * * *